(12) United States Patent
Chana et al.

(10) Patent No.: US 9,980,735 B2
(45) Date of Patent: May 29, 2018

(54) FORCE SENSING DISTAL FEMORAL ALIGNMENT SYSTEM AND METHOD OF USE

(71) Applicant: Synvasive Technology, Inc., El Dorado Hills, CA (US)

(72) Inventors: Barjinder S. Chana, Reno, NV (US); Michael G. Fisher, Reno, NV (US); Michael Haight, Sacramento, CA (US); Leo Beckers, Grimbergen (BE)

(73) Assignee: Synvasive Technology, Inc., El Dorado Hills, CA (US)

( * ) Notice: Subject to any disclaimer, the term of this patent is extended or adjusted under 35 U.S.C. 154(b) by 209 days.

(21) Appl. No.: 14/692,117

(22) Filed: Apr. 21, 2015

(65) Prior Publication Data

US 2015/0230804 A1    Aug. 20, 2015

Related U.S. Application Data

(63) Continuation of application No. 12/609,666, filed on Oct. 30, 2009, now abandoned.

(Continued)

(51) Int. Cl.
*A61B 17/15* (2006.01)
*A61B 17/02* (2006.01)
*A61B 19/00* (2006.01)

(52) U.S. Cl.
CPC .......... *A61B 17/155* (2013.01); *A61B 17/025* (2013.01); *A61B 2017/0268* (2013.01); *A61B 2019/464* (2013.01)

(58) Field of Classification Search
CPC .................................................. A61B 17/155
See application file for complete search history.

(56) References Cited

U.S. PATENT DOCUMENTS

| 4,501,266 A | 2/1985 | McDaniel |
| 5,116,338 A | 5/1992 | Poggie et al. |

(Continued)

FOREIGN PATENT DOCUMENTS

| WO | WO-2005037121 A1 | 4/2005 |
| WO | WO-2005089681 A2 | 9/2005 |
| WO | WO-2006047005 A2 | 5/2006 |

OTHER PUBLICATIONS

"U.S. Appl. No. 13/524,405, Advisory Action dated Oct. 7, 2015", 3 pgs.

(Continued)

*Primary Examiner* — Andrew Yang
(74) *Attorney, Agent, or Firm* — Schwegman Lundberg & Woessner, P.A.

(57) ABSTRACT

Devices, systems, and methods are provided for facilitating the aligning and balancing of the knee during total knee replacement surgery. A femoral assembly is engaged with a distal femur. The positions of medial and lateral portions of the femoral assembly relative to a stationary portion of the femoral assembly can be separately adjusted to adjust the alignment of the knee. A force sensor will be provided to sense the forces in the medial and lateral portions of the knee, and the medial and lateral portions of the femoral assemblies will be adjusted so that the sensed forces are balanced. The alignment of the knee is visually verified using a knee alignment verification member coupled to the femoral assembly. The knee alignment verification member may emit laser beams along the mechanical axes of the femur and tibia, or the knee alignment verification member may couple to alignment rods aligned along these axes.

21 Claims, 37 Drawing Sheets

Related U.S. Application Data

(60) Provisional application No. 61/109,770, filed on Oct. 30, 2008.

(56) References Cited

U.S. PATENT DOCUMENTS

| | | | |
|---|---|---|---|
| 5,213,112 A | 5/1993 | Niwa et al. | |
| 5,470,354 A | 11/1995 | Hershberger et al. | |
| 5,540,696 A | 7/1996 | Booth, Jr. et al. | |
| 5,597,379 A | 1/1997 | Haines et al. | |
| 5,656,785 A | 8/1997 | Trainor et al. | |
| 5,669,914 A | 9/1997 | Eckhoff | |
| 5,733,292 A | 3/1998 | Gustilo et al. | |
| 5,800,438 A | 9/1998 | Tuke et al. | |
| 5,860,980 A | 1/1999 | Axelson, Jr. et al. | |
| 5,911,723 A | 6/1999 | Ashby et al. | |
| 6,022,377 A | 2/2000 | Nuelle et al. | |
| 6,575,980 B1 | 6/2003 | Robie | |
| 6,758,850 B2 | 7/2004 | Smith et al. | |
| 7,104,996 B2 | 9/2006 | Bonutti | |
| 7,442,196 B2 | 10/2008 | Fisher et al. | |
| 7,578,821 B2 | 8/2009 | Fisher et al. | |
| 8,323,290 B2 * | 12/2012 | Metzger | A61B 17/025 606/90 |
| 9,439,656 B2 | 9/2016 | Chana et al. | |
| 2005/0209605 A1 | 9/2005 | Grimm et al. | |
| 2005/0240196 A1 | 10/2005 | Davis et al. | |
| 2005/0267485 A1 | 12/2005 | Cordes et al. | |
| 2006/0241569 A1 | 10/2006 | Disilvestro | |
| 2007/0219559 A1 | 9/2007 | Heavener et al. | |
| 2007/0232959 A1 | 10/2007 | Couture et al. | |
| 2007/0244488 A1 | 10/2007 | Metzger et al. | |
| 2010/0063508 A1 | 3/2010 | Borja et al. | |
| 2010/0198275 A1 | 8/2010 | Chana et al. | |
| 2012/0259342 A1 | 10/2012 | Chana et al. | |
| 2017/0042554 A1 | 2/2017 | Chana et al. | |

OTHER PUBLICATIONS

"U.S. Appl. No. 13/524,405, Examiner Interview Summary dated Sep. 24, 2015", 3 pgs.

"U.S. Appl. No. 13/524,405, Final Office Action dated Jul. 30, 2015", 8 pgs.

"U.S. Appl. No. 13/524,405, Notice of Allowance dated May 17, 2016", 7 pgs.

"U.S. Appl. No. 13/524,405, Response filed Sep. 24, 2015 to Final Office Action dated Jul. 30, 2015", 9 pgs.

"U.S. Appl. No. 12/609,666, Advisory Action dated Dec. 19, 2013", 3 pgs.

"U.S. Appl. No. 12/609,666, Examiner Interview Summary dated May 23, 2013", 3 pgs.

"U.S. Appl. No. 12/609,666, Final Office Action dated Feb. 26, 2015", 10 pgs.

"U.S. Appl. No. 12/609,666, Final Office Action dated Oct. 4, 2013", 10 pgs.

"U.S. Appl. No. 12/609,666, Non Final Office Action dated Feb. 14, 2013", 12 pgs.

"U.S. Appl. No. 12/609,666, Non Final Office Action dated Jun. 26, 2014", 9 pgs.

"U.S. Appl. No. 12/609,666, Non Final Office Action dated Oct. 11, 2012", 10 pgs.

"U.S. Appl. No. 12/609,666, Response filed Jan. 6, 2014 to Advisory Action dated Dec. 19, 2013", 10 pgs.

"U.S. Appl. No. 12/609,666, Response filed Jan. 11, 2013 to Non Final Office Action dated Oct. 11, 2012", 14 pgs.

"U.S. Appl. No. 12/609,666, Response filed May 14, 2013 to Non Final Office Action dated Feb. 14, 2013", 12 pgs.

"U.S. Appl. No. 12/609,666, Response filed May 22, 2012 to Restriction Requirement dated May 11, 2012", 2 pgs.

"U.S. Appl. No. 12/609,666, Response filed Oct. 27, 2014 to Non-Final Office Action dated Jun. 26, 2014", 11 pgs.

"U.S. Appl. No. 12/609,666, Response filed Dec. 4, 2013 to Final Office Action dated Oct. 4, 2013", 10 pgs.

"U.S. Appl. No. 12/609,666, Restriction Requirement dated May 11, 2012", 8 pgs.

"U.S. Appl. No. 13/524,405, Non Final Office Action dated Dec. 31, 2014", 8 pgs.

"U.S. Appl. No. 13/524,405, Response filed Mar. 31, 2015 to Non-Final Office Action dated Dec. 31, 2014", 8 pgs.

"U.S. Appl. No. 13/524,405, Response filed Aug. 4, 2014 to Restriction Requirement dated Jun. 4, 2014", 12 pgs.

"U.S. Appl. No. 13/524,405, Restriction Requirement dated Jun. 4, 2014", 9 pgs.

"European Application Serial No. 09824192.0, Extended European Search Report dated Mar. 21, 2014", 7 pgs.

"European Application Serial No. 09824192.0, Response filed Oct. 20, 2014 to Extended European Search Report dated Mar. 21, 2014", 18 pgs.

"International Application Serial No, PCT/US2009/062846, International Preliminary Report on Patentability dated May 3, 2011", 9 pgs.

"International Application Serial No. PCT/US2009/062846, International Search Report dated Jan. 13, 2010", 4 pgs.

"International Application Serial No. PCT/US2009/062846, Written Opinion dated Jan. 13, 2010", 8 pgs.

"International Application Serial No. PCT/US2009/061941, International Search Report dated Dec. 18, 2009", 1 pg.

Albee, Fred H. "Bone Surgery With Machine Tools", Scientific American vol. 154.4, (Apr. 1936), 178-181.

Eckhoff, D. G, et al., "Three-Dimensional Morphology and Kinematics of the Distal Part of the Femur Viewed in Virtual Reality", Journal of Bone & Joint Surgery, vol. 85-A, Supplement 4, (2003), 97-104.

Mihalko, W. H, et al., "Comparison of Ligament-Balancing Techniques During Total Knee Arthroplasty", Journal of Bone & Joint Surgery, vol. 85-A, Supplement 4, (2003), 132-135.

Murray, D. G, et al., "Variable Axis Total Knee Surgical Technique", Howmedica Surgical Techniques, Howmedica, Inc., (1977), 2-7.

Ries, M. D, et al., "Soft-Tissue Balance in Revision Total Knee Arthroplasty", Journal of Bone & Joint Surgery, vol. 85-A, Supplement 4,, (2003), 38-42.

U.S. Appl. No. 15/239,029, filed Aug. 17, 2016, System for Positioning a Cutting Guide in Knee Surgery.

"U.S. Appl. No. 15/239,029, Preliminary Amendment filed Feb. 22, 2017", 7 pgs.

* cited by examiner

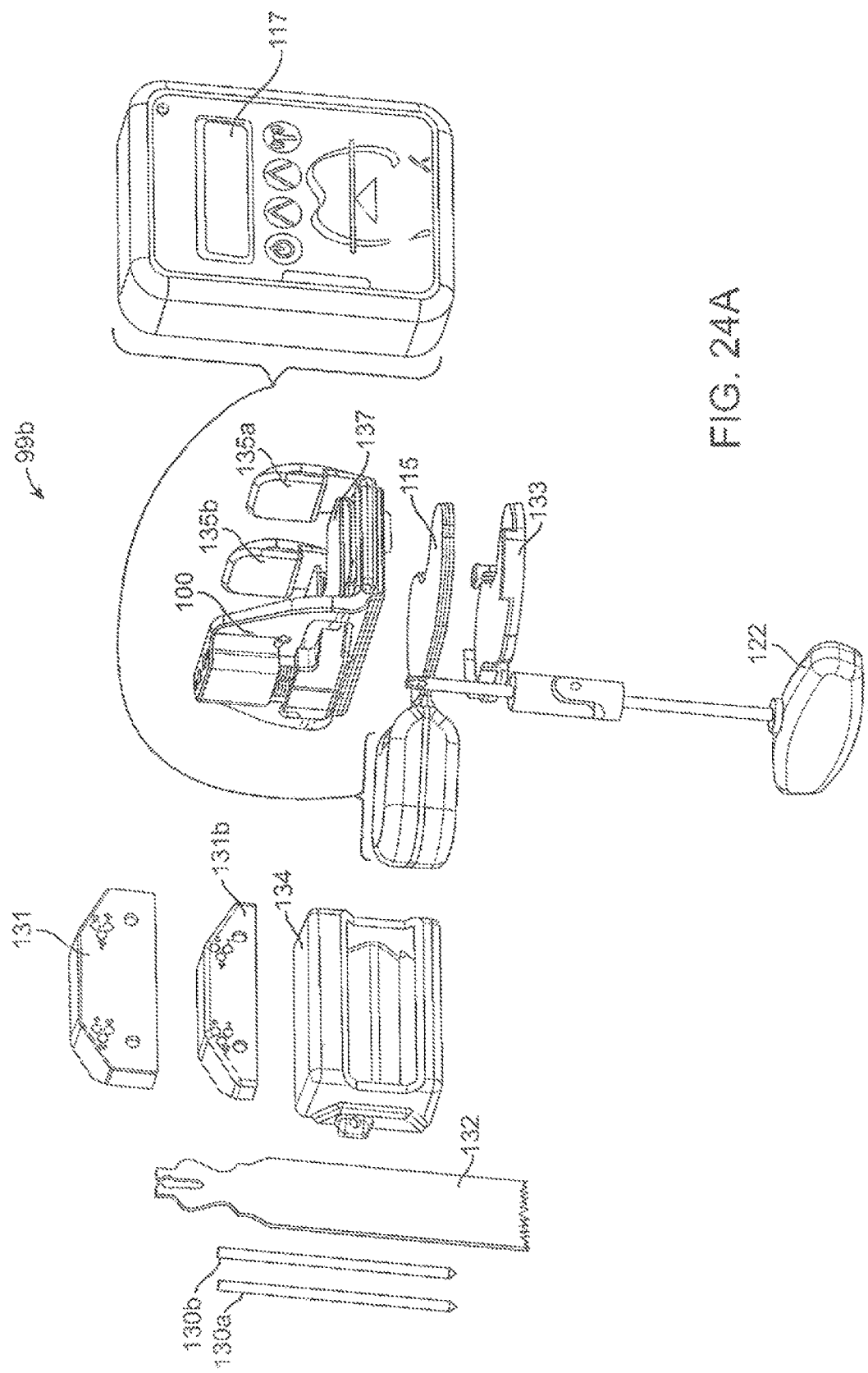

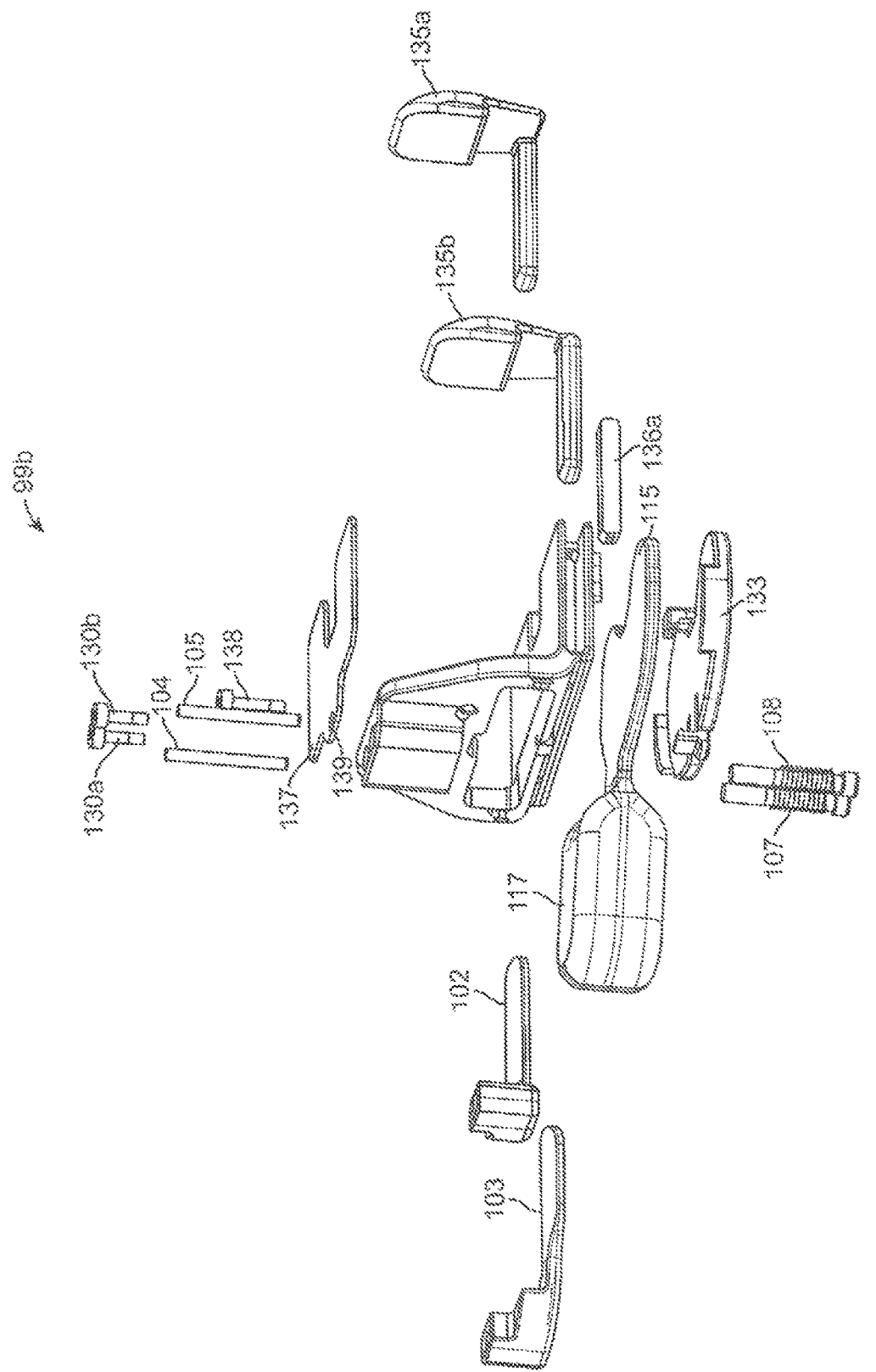

FORCE SENSING DISTAL FEMORAL ALIGNMENT SYSTEM AND METHOD OF USE

CROSS-REFERENCE TO RELATED APPLICATIONS

The present application is a continuation of U.S. application Ser. No. 12/609,666, filed Oct. 30, 2009, which is a non-provisional of, and claims the benefit of priority under 35 U.S.C. § 119(e), U.S. Provisional Application No. 61/109,770 filed Oct. 30, 2008, the entire contents of which are incorporated herein by reference.

BACKGROUND OF THE INVENTION

1. Field of Invention

The present invention relates generally to medical surgical devices, systems, and methods. More specifically, the invention relates to devices, systems and methods for facilitating knee surgery procedures, in particular, knee replacement procedures.

The knee is generally defined as the point of articulation of the femur with the tibia. Structures that make up the knee include the distal femur, the proximal tibia, the patella, and the soft tissues within and surrounding the knee joint, the soft tissues including the ligaments of the knee. The knee is generally divided into three compartments: medial (the inside part of the knee), lateral (the outside part of the knee), and patello-femoral (the joint between the kneecap and the femur). The medial compartment comprises the medial joint surfaces of the femur, tibia, and the meniscus wedged therebetween. The lateral compartment comprises the lateral joint surfaces of the femur, tibia, and the meniscus wedged therebetween. The patellofemoral compartment comprises the joint between the undersurface of the kneecap or patella and the femur. Four ligaments are especially important in the stability, alignment and functioning of the knee—the anterior cruciate ligament, the posterior cruciate ligament, the medial collateral, ligament, and the lateral collateral ligament. In an arthritic knee, protective cartilage at the point of articulation of the femur with the tibia is often worn away, allowing the femur to directly contact the tibia. This bone-on-bone contact can cause significant pain, discomfort, and disability for a patient and will often necessitate knee replacement or knee arthroplasty.

Knee arthroplasty involves replacing the diseased and painful joint surface of the knee with metal and plastic components shaped to allow natural motion of the knee. Knee replacement may be total or partial. Total knee replacement surgery, also referred to as total knee arthroplasty ("TKA"), involves a total replacement of the distal end of the femur, the proximal end of the tibia, and often the inner surface of the patella with prosthetic parts. Cuts are made on the distal, end of the femur and the proximal end of the tibia. Prosthetic parts are then attached. The prosthetic parts create a stable knee joint that moves through a wide range of motion. The replacement of knee structures with prosthetic parts allows the knee to avoid bone-on-bone contact and provides smooth, well-aligned surfaces for joint movement.

In knee replacement surgeries, it is often vital to restore the mechanical alignment of the knee, i.e., the proper alignment of the mechanical axes of the femur and tibia with each other. Many methods and devices currently are used to restore the mechanical alignment of the leg. These methods and devices are typically used during Total Knee Replacement surgery and include alignment rods, e.g., intramedullary and extramedullary rods, surgical navigation systems, and CT and or MRI based "bone morphing" or "shape-fitting" technologies. Generally, empirical anatomical landmarks are used in these methods. These anatomical landmarks are either directly/mechanically observed intraoperatively, or indirectly relied upon, serving as the foundation of a computer generated reference method. Reference geometry and physical or virtual measurements are often used to ultimately align bone-cutting guides or templates which facilitate bone resections (made with a surgical saw blade). These bone resections will typically properly orient a knee prosthesis in the correct location/alignment. Generally, none of these methods directly take the condition or tendencies of the soft-tissue structures, such, as the lateral collateral and medial collateral ligaments, about the knee into consideration.

Historically, surgeons performing total knee replacement surgery in the late 1970s and early 1980s, would typically first resect the proximal tibia, creating a flat surface perpendicular to the shaft of the tibia. The leg was then brought to extension. Spacer blocks were shoved between the resected tibia and the uncut distal femur. The spacer blocks were selected from various thicknesses in order to distract the knee joint space to the extent the ligaments about the knee were somewhat taut. Once the knee joint was distracted to that taut condition, a distal femoral cutting guide was positioned in a way to yield a distal femoral bone cut parallel to the tibial cut. It was believed then, a distal femoral bone cot using this method, of distracting the joint space between the tibia and femur, would yield proper alignment of the mechanical axis of the leg. This method would often prove successful as practiced by a skilled surgeon and in the case of "passive deformities" of the knee. However, the distraction method would typically not have any accurate means of determining ligament forces between the medial side of the knee and/or the lateral side of the knee. As such, proper alignment would often not be restored. Additionally, the method of first making a proximal tibial bone resection and then making a distal femoral bone resection parallel to the tibial bone resection did not restore proper alignment of the leg in the case of "fixed deformities" of the knee. The case of "fixed deformities" of the knee would otherwise require ligament releases to restore proper-alignment of the knee. Accordingly, many early knee replacement surgeons determined the tibial bone resection and the distal femoral bone resections should be made independent of each other.

As technology has advanced, including the introduction of CT scanners and MRI technology, the thought of computerized bone morphing has gained popularity as a means to accurately place cutting guides. The cutting guides in turn would be used in efforts to place prosthetic knee implants in a position m which the knee is properly aligned. Early studies have not found these hone morphing technologies always accurate, reporting proper alignment of the leg was not restored. However, a proper patient selection, e.g., patients with mild passive deformities of the knee, might be viable candidates for bone morphing technology, assuming those patients/deformities could be properly corrected by simple anatomical referencing, as determined by a CT or MRI scan.

However, bone morphing technology is often, costly, requiring a CT or MRI scan to determine any given patients anatomy. Electronic images from such scans must be "filtered" by a computer technician. The "filtered" scan data must be electronically conveyed to some type of fabrication machine, such as a CNC Machining Center or a Rapid Prototype Machine. Ultimately, "shape-matching" and "patient specific" cutting guides must be produced and delivered into surgery.

As such, there is a clear need for systems, devices, and methods of knee surgery that can help surgeons quickly, accurately, and cost-effectively position, the distal femoral, cutting guide, thus restoring proper alignment and soft-tissue balance of the leg during total knee replacement surgery.

2. Description of Background Art

Non-patent literature which may be of interest may include: Murray, David G., "Variable Axis™ Total Knee Surgical Technique," Howmedica Surgical Techniques, Bowmedica Inc. 1977; Mihaiko, W H et at, "Comparison of Ligament-Balancing Techniques Dining Total Knee Arthroplasty," Jnl. Bone & Jt. Surg., Vol. 85-A Supplement 4, 2003, 132-135; Eckhoff, D G et al., "Three-Dimensional Morphology and Kinematics of the Distal Part of the Femur Viewed in Virtual Reality, Jnl. Bone & Jt, Surg., Vol 85-A Supplement 4, 2003, 97-104; and Ries, M D, et al., "Soft-Tissue Balance in Revision Total Knee Arthroplasty," Jnl. Bone & Jt, Surg., Vol 85-A Supplement 4, 2003, 38-42. Patents of interest may include U.S. Pat. Nos. 4,501,266; 4,646,729; 4,703,751; 4341,975; 5,116,338; 5,417,694; 3,540,696; 5,597,379; 5,720,752; 5,733,292; 5,800,438; 5,860,980; 5,911,723; 6,022,377 and 6,758,850. Patents applications of interest may include co-assigned U.S. patent application Ser. No. 10/773,608, now U.S. Pat. No. 7,442,196, entitled "Dynamic Knee Balancer"; Ser. No. 10/973,936, now U.S. Pat. No. 7,578,821 entitled "Dynamic Knee Balancer with Pressure Sensing"; Ser. No. 11/149,944 now U.S. Patent Publication Application No. 2005/0267485 A1 entitled "Dynamic Knee Balancer with Opposing Adjustment Mechanism"; 61/090,535 entitled "Sensing Force During Partial and Total Knee Replacement Surgery"; and 61/107, 973 entitled "Dynamic Knee Balancing for Revision Procedures", the entire contents of each of which are incorporated herein by reference.

BRIEF SUMMARY OF THE INVENTION

The present invention provides devices, systems, and methods for facilitating a surgery performed, on a knee, particularly by facilitating the aligning of the knee during a total knee replacement surgery. A femoral assembly is engaged with a distal femur and placed in the gap between the distal femur and proximal tibia. The femoral assembly comprises a stationary portion, an adjustable medial portion, and an adjustable lateral femoral portion. The positions of the medial and lateral femoral portions relative to the stationary portion can be separately adjusted to adjust, the varus-valgus alignment, of the knee, e.g., the angle between the femur and tibia, as well as the tension in the soft tissues adjacent the knee. Additionally, the femoral assembly comprises adjustable posterior members that fill the posterior capsule of the knee with, a thickness similar to the prosthetic femoral implant. Typically, a force sensor will be provided to sense the forces in the medial portion of the knee and the lateral portion of the knee, and the medial and lateral femoral portions will be adjusted so that the sensed forces are balanced. A visual display may be provided to show the surgeon the sensed forces. In addition, a thickness adapter may be provided to removable attach to the force sensor to fill the space between the femur and tibia to the point force readings are obtained. The alignment of the knee ears be visually verified using a knee alignment verification member coupled to the femoral assembly, and further verified by angular graduation markings placed upon the femoral stationary portion. The knee alignment verification member may emit laser beams along the mechanical axes of the femur and tibia. Or, alignment rods which align along the mechanical axes of the femur and tibia may be coupled to the knee alignment verification member. The alignment of the knee can be verified using with the laser beams and/or the alignment rods. When the knee is properly aligned, placement pins may be positioned in the distal femur guided by the femoral assembly. The femoral assembly can then be removed and a cutting guide can be positioned on the distal femur based on the position of the placement pins. A cut parallel to a previously made cut on the tibia can then be made on the distal femur. A prosthetic knee placed on these cuts will maintain the proper alignment of the knee.

In a first aspect, the invention provides a system for aligning the knee during a surgical procedure on the knee. The system comprises a femoral assembly that is removably engaged with a distal, femur. The femoral, assembly includes a stationary femoral portion, an adjustable medial femoral portion (which is coupled to the stationary femoral portion), and an adjustable lateral femoral portion (which is coupled to the stationary femoral portion. A knee alignment verification member is coupled with the stationary femoral portion of the femoral assembly and provides visual confirmation of a femoral and tibial mechanical axes of the knee. A force sensor is coupled with the stationary femoral portion of the femoral assembly. The force sensor comprises a medial portion for sensing a first force in a medial portion of the knee and a lateral portion for sensing a second force in a lateral portion of the knee.

In one embodiment, the knee alignment verification member means includes a laser knee alignment verification member is coupled to the stationary femoral portion. The laser knee alignment provides a first laser beam oriented along the femoral axis of the knee and a second laser beam oriented along the tibial axis of the knee.

In some embodiments, the knee alignment verification member includes a mechanical knee alignment verification assembly. The mechanical knee alignment verification assembly includes a knee alignment hub. A first rod is coupled with the knee alignment hub to be oriented along the femoral axis of the knee and a second rod is coupled with the knee alignment hub to be oriented along the tibial axis of the knee.

In an embodiment, the adjustable medial portion includes a medial paddle and the adjustable femoral portion includes a lateral paddle.

In still other embodiments, the position of the adjustable medial femoral portion relative to the stationary femoral portion is adjustable. The position of the adjustable lateral femoral portion relative to the stationary femoral portion is adjustable.

In other embodiments, the adjustable medial femoral portion and the adjustable lateral femoral portion are separately adjustable.

In some embodiments, a medial rotatable screw couples the adjustable medial femoral portion, with the stationary femoral portion. A lateral rotatable screw couples the adjustable lateral femoral portion with the stationary femoral portion.

In some embodiments, rotating the medial rotatable screw adjusts the position, of the adjustable medial femoral portion relative to the stationary femoral portion. Rotating, the lateral rotatable screw adjusts the position of the adjustable lateral femoral portion relative to the stationary femoral portion.

In some embodiments, the force sensor comprises a force sensing element selected from the group consisting of piezoelectric sensors, force sensing resistors, force sensing capacitors, strain gages, load cells, and pressure sensors.

In still other embodiments, a processor is coupled with the force sensor for processing sensed force data into usable data and for providing the data to a user. A visual display is coupled with the processor and adapted to display the usable data.

In some embodiments, the visual display displays usable data representing a first force sensed in the medial portion of the knee and a second force sensed in the lateral portion of the knee.

In some embodiments, the system for aligning a knee during knee surgery includes a plurality of locating pins. The stationary femoral portion defines at least one medial aperture for positioning at least one locating pin on the distal femur and at least one lateral aperture for positioning at least a second locating pin on the distal femur.

In some embodiments of the invention, a cutting guide is removably engaged with the distal femur. The cutting guide is positioned relative to the distal, femur based on the position of at least one first locating pin and the at least a second locating pin.

In some embodiments, the force sensor is removably coupled to a thickness adapter. The adapter fills the space between the femur and tibia.

In some embodiments, the adjustable medial femoral portion and the adjustable lateral femoral portion include a medial fulcrum and lateral fulcrum. The fulcrums are positioned against the provisionally out distal femur when the distal femoral alignment assembly is mounted against the distal femur. In other embodiments, a bone interface plate is disposed between the fulcrums and the distal lemur.

In a second aspect, the invention provides a method for aligning the knee during a surgical procedure on the knee including engaging a femoral assembly with a distal femur. The femoral assembly includes a stationary femoral portion, an adjustable medial femoral portion (coupled to the stationary femoral portion), and an adjustable lateral femoral portion (coupled to the stationary femoral portion). A force sensor is coupled with the stationary femoral portion of the femoral assembly. A first force is sensed in a medial portion of the knee and a second force is sensed in the lateral portion of the knee using the coupled force sensor. The position of the adjustable medial femoral portion can be adjusted separately relative to the stationary femoral portion and the position of the adjustable lateral femoral portion is separately adjustable relative to the stationary femoral portion based on the sensed first and second forces to align a femoral and tibial mechanical axes of the knee. The alignment of the femoral and tibial mechanical axes of the knee are visually confirmed using a knee alignment verification assembly coupled with the stationary femoral portion of the femoral assembly.

In one embodiment, a method for aligning the knee dining a surgical procedure on the knee comprises coupling a mechanical knee alignment verification assembly with the stationary femoral member of the femoral assembly. A first alignment rod of the mechanical knee alignment verification assembly is aligned, along the femoral axis of the knee and a second alignment rod of the mechanical knee alignment verification assembly is aligned along the tibial axis of the knee. The femoral and tibial mechanical axes of the knee is visually confirmed by the alignment of the first alignment rod and the second alignment rod relative to each other.

In another embodiment, a laser knee alignment verification member is coupled with the stationary femoral member of the femoral assembly. A first laser beam from the laser knee alignment verification member is aligned along the femoral mechanical axis of the knee and a second laser beam from the laser knee alignment verification member is aligned along the tibial mechanical axis of the knee along the tibial axis of the knee. The alignment of the femoral and tibial mechanical axes of the knee is visually confirmed by the alignment of the first laser beam and the alignment of the second laser beam relative to each other.

In some embodiments, the positions of the adjustable medial femoral portion relative to the stationary femoral portion and of the adjustable lateral femoral portion relative to the stationary femoral portion are adjusted based on the sensed first force and the sensed second force so that the first and second forces are balanced.

In some embodiments, the first force in a medial portion of the knee is sensed and a second force in a lateral portion of the knee is sensed using the coupled force sensor. This includes transmitting a voltage to a sensor element of a thin force-sensing portion of the force sensor and measuring the voltage after it has passed through the sensor element. The percentage of the voltage that passed through the sensor element is determined relative to the voltage transmitted to the sensor element. The measured force is derived from the percentage.

In yet another embodiment, the sensed first force and the sensed second force is visually displayed by a display coupled to the force sensor.

In some embodiments, separately adjusting the position of the adjustable medial femoral portion relative to the stationary femoral portion and the position of the adjustable lateral femoral, portion relative to the stationary femoral portion comprises rotating at least one of a lateral rotatable screw coupling the adjustable lateral femoral portion to the stationary femoral portion and a medial rotatable screw coupling the adjustable medial femoral portion to the stationary femoral portion.

In some embodiments, the stationary femoral portion defines at least one medial aperture and at least one lateral aperture. The method further includes positioning at least one locating pin on the distal femur based on at least one medial aperture and positioning at least a second locating pin on the distal femur based on the at least one lateral aperture.

In an embodiment, the femoral assembly is disengaged with the distal femur and engages a distal femoral cutting guide with the distal femur. The distal femoral cutting guide is positioned relative to the distal femur based on the position of at least one first and at least one second locating pins.

In some embodiments, cuts are made on the distal femur based on the position of the distal femoral cutting guide.

In another aspect, the invention provides a method for aligning a leg during knee surgery. The leg has a femur and a tibia. The femur has a mechanical axis, a distal end and a proximal end. The tibia has a mechanical axis, a distal end and a proximal end. The method of aligning the leg includes engaging a femoral assembly with the provisionally cut distal end of the femur. The femoral assembly includes a stationary femoral portion, an adjustable medial femoral portion that has a medial pivot fulcrum coupled to the stationary femoral portion, and an adjustable lateral femoral portion that has a lateral pivot fulcrum coupled to the stationary femoral portion. A force sensor is coupled with the stationary femoral portion of the femoral assembly. A medial posterior member is reversibly coupled to the medial side of the stationary femoral portion. A lateral posterior member is reversibly coupled to the lateral side of the stationary femoral portion. The medial member abuts the medial posterior femur and the lateral member abuts the lateral posterior femur. A first force is sensed in a medial portion of the knee and a second force is sensed in the lateral portion of the knee using the force sensor. The position of the adjustable medial femoral portion is adjusted relative to the stationary femoral portion and the position of the adjustable lateral femoral portion is (separately) adjusted relative to the stationary femoral portion based on the sensed first and second forces to align the femoral and tibial mechanical axes of the knee. The alignment of the femoral and tibial mechanical axes of the knee is visually confirmed using a knee alignment verification assembly which is coupled with the stationary femoral portion of the femoral assembly.

In one embodiment, the medial member abuts the medial posterior femur and the lateral member abuts the lateral posterior femur when the leg is folly extended.

In some embodiments, the medial and lateral fulcrums determine fixed distance points to adjust an angle.

In some embodiments, a bone interface plate is disposed between the adjustable medial and lateral femoral portions and the distal femur.

BRIEF DESCRIPTION OF THE DRAWINGS

FIG. 24A-B shows exploded views of a knee alignment system according to embodiments of the invention.

DETAILED DESCRIPTION OF THE INVENTION

Embodiments of the present invention provide systems, devices, and methods for facilitating the alignment and balancing of the knee dining knee replacement surgery and verifying such balance and alignment. Once the knee is properly aligned, a cut parallel to a previously made cut on the tibia can be made on the distal femur. A prosthetic knee placed on these cuts will maintain the proper alignment of the knee.

Figure 1:
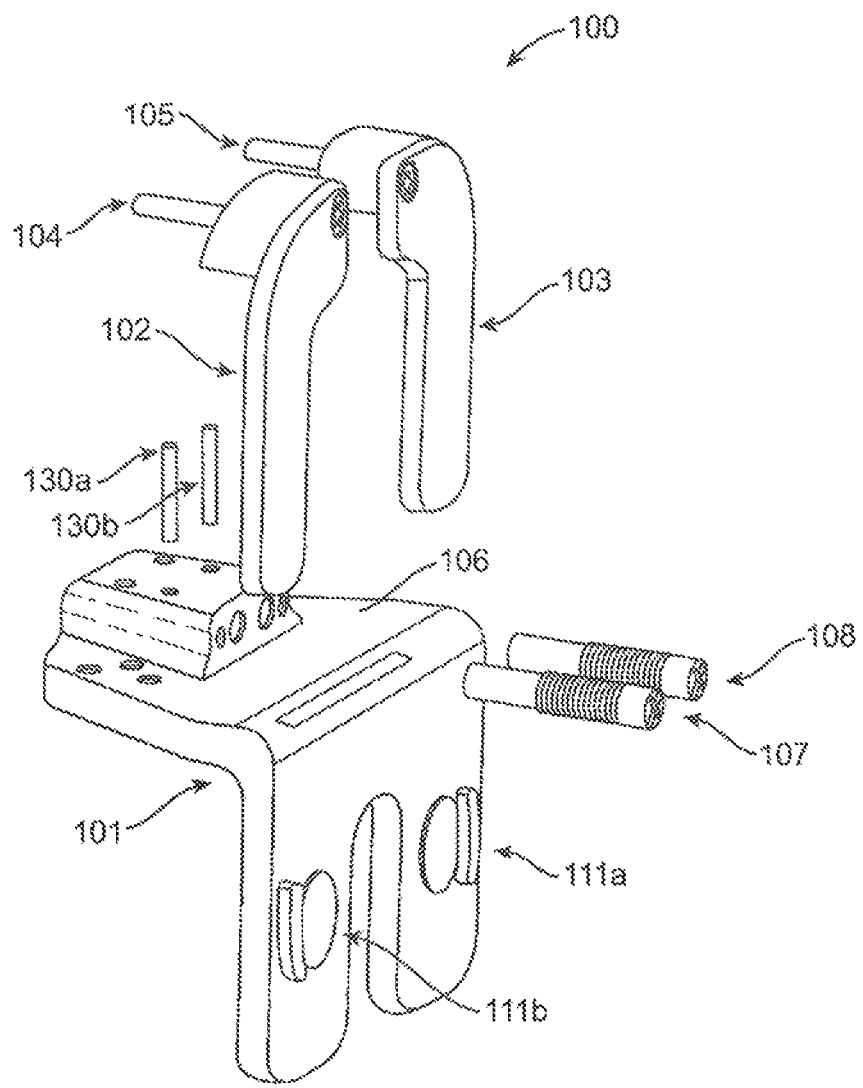
FIG. 1 shows an exploded view of a distal femoral alignment component assembly according to embodiments of the invention.

Referring now to FIG. 1, a distal femoral alignment assembly or component 100 according to embodiments of the invention is shown in an exploded view. As shown in FIG. 1, distal femoral alignment assembly 100 can be used for either the left or right knee, i.e., one side of the distal femoral alignment assembly may be the medial side while the other is the lateral side and vice versa. Distal femoral alignment assembly 100 comprises a main body 101, an adjustable medial femoral portion coupled to the main body, and an adjustable lateral femoral portion coupled to the main body. When the distal femoral alignment assembly 100 is coupled to a distal femur, the main body or stationary portion of the distal femoral alignment assembly is generally stationary with respect to the adjustable medial and lateral femoral portions. The adjustable medial and lateral femoral portions are adjusted with respect to the main body. Adjustable medial and lateral femoral portions respectively comprise medial and lateral paddles 102, 103. The medial and lateral paddles each comprise anti-rotation shafts 104, 105 which fit into slots 106 of the main body. Medial and lateral distraction screws 107, 108 respectively couple the medial and lateral paddles 102, 103 with the main body 101. Distraction-screw capture pegs 109, 110 fix the axial position of the distraction screws 107, 108 relative to the main, body 101 such that rotation of the medial and lateral distraction screws only adjusts the positions of the adjustable medial and lateral femoral portions with respect to the main body 101. The main body comprises mounts for attachment of a force sensor 111.

Figure 2:
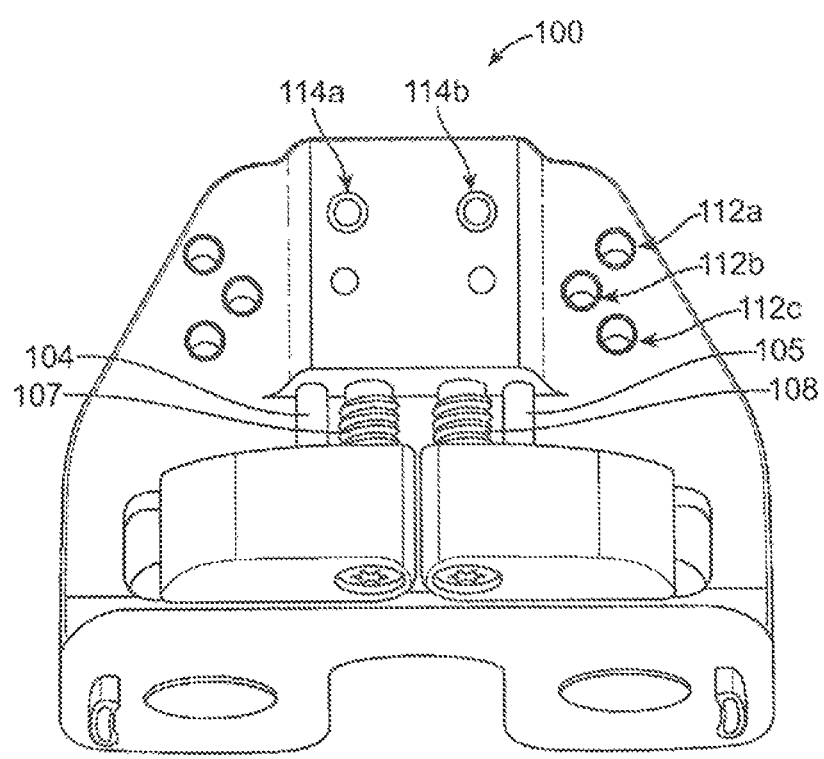
FIG. 2 shows a top view of the unadjusted distal femoral alignment assembly of FIG. 1.

Referring now to FIG. 2, the main body 101 of the distal femoral adjustment assembly 100 further defines cutting guide locating apertures on its medial 113a-c and lateral 112a-c sides. These apertures are cutting guide locating means, e.g., by facilitating the placement of placement pins from which provide points of reference for the placement of a cutting guide. The main body further defines slots or verification attachment slots or apertures 114a, 114b for attaching a knee alignment verification means as described below.

Figure 3:
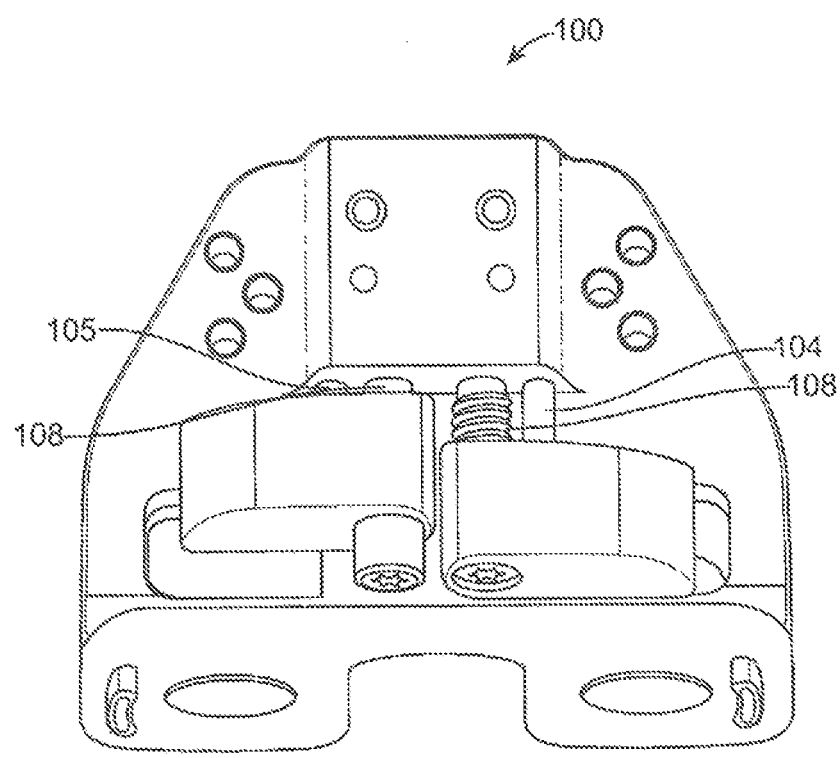
FIG. 3 shows a top view of the adjusted distal femoral alignment assembly of FIG. 1.
Figure 4:
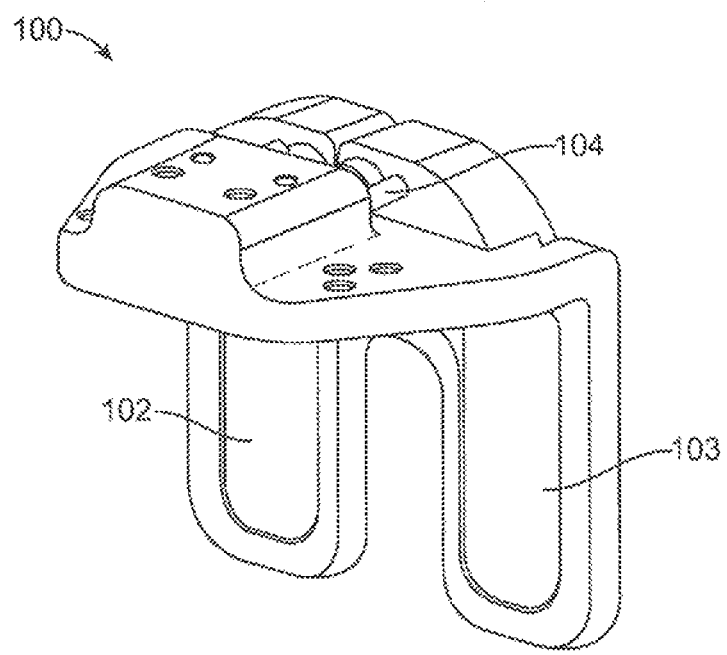
FIG. 4 shows a perspective view of the unadjusted distal femoral alignment assembly of FIG. 1.
Figure 5:
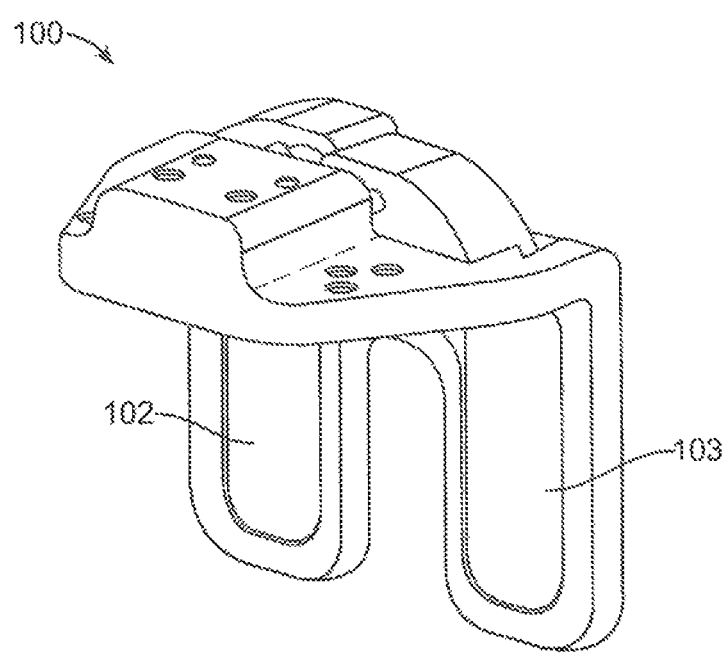
FIG. 5 shows a perspective view of the adjusted distal femoral alignment assembly of FIG. 1.

FIGS. 2 and 4 show the distal femoral adjustment assembly 100 unadjusted. FIGS. 3 and 5 show the distal femoral adjustment assembly 100 adjusted, i.e., the position of one paddle of the distal femoral adjustment assembly has been moved relative to the other.

Figure 6:
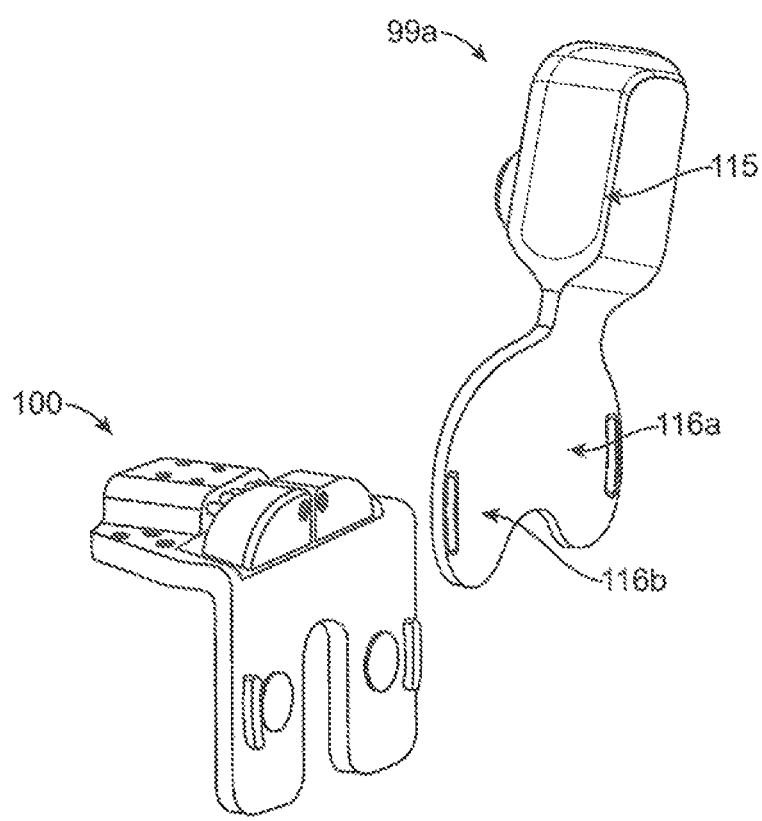
FIGS. 6 and 7 shows perspective views of a knee alignment system according to embodiments of the invention.
Figure 7:
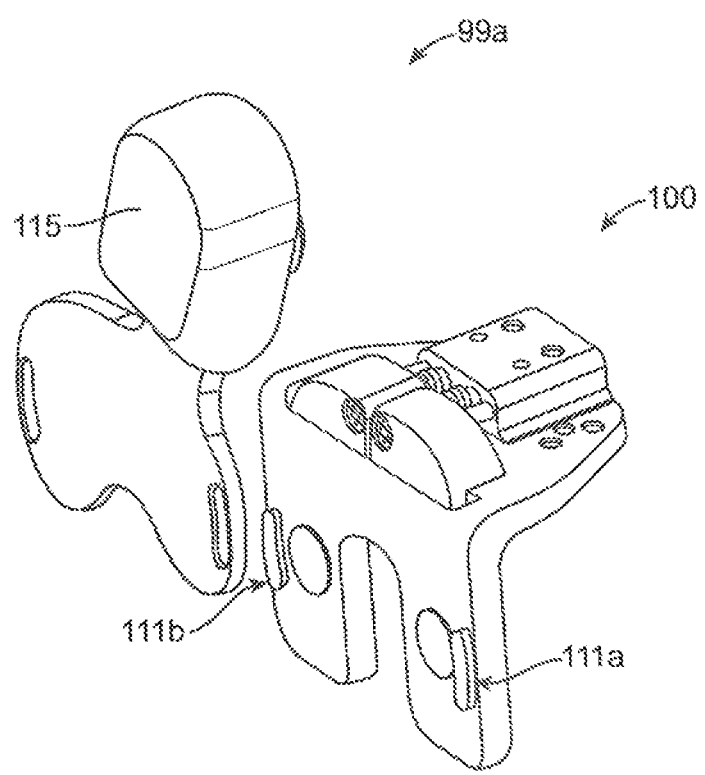

FIGS. 6 and 7 show a perspective view of a knee alignment system 99a according to embodiments of the invention. The system comprises the distal femoral adjustment assembly 100 as described above. The system further comprises a electronic force-sensing means or force sensor 115 coupleable with the distal femoral adjustment assembly 100. As shown, the force sensor 115 comprises a handheld tool hot may alternatively be a smaller device coupleable with the main body of the distal femoral adjustment assembly 100. The force sensor 115 senses the force between me medial portion of the distal femur and the medial portion of the tibial plateau as well as the force between the lateral portion of the distal femur and the lateral portion of the tibial plateau, for example, by comprising first and second force sensing portions 116a, 116b, the first force sensing portion 116a being a lateral force sensing portion while the second 116b is a medial force sensing portion and vice versa. The distal femur and tibial plateau are not shown in FIGS. 6-7. The force sensor 115 may be similar to those described U.S. patent applications Ser. No. 61/090,535 entitled "Sensing Force During Partial and Total Knee Replacement Surgery" and 61/107,973 entitled "Dynamic Knee Balancing for Revision Procedures", the entireties of which had been previously incorporated herein by reference.

Figure 8:
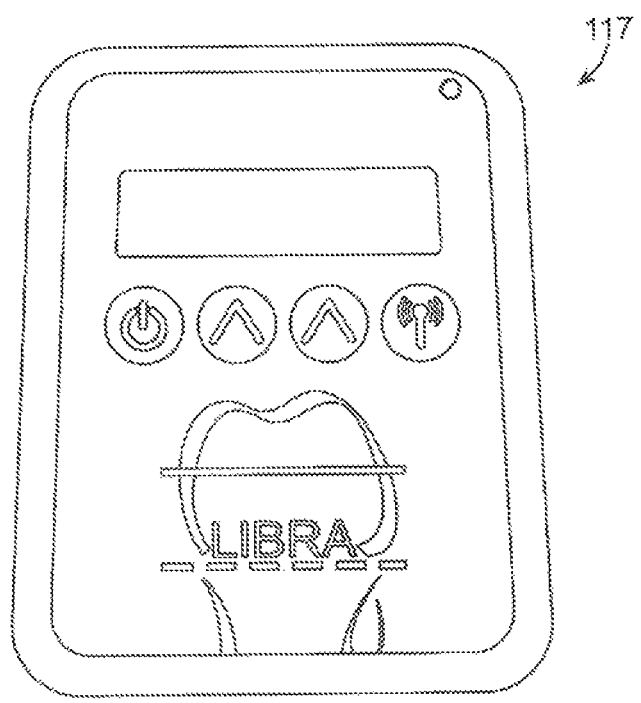
FIG. 8 shows a visual display of a knee alignment system according to embodiments of the invention.

FIG. 8 shows a visual display 117 coupleable with the force sensor 115. The visual display displays date representative of the force sensed by the force sensor and may be similar to those described in U.S. patent application Ser. No. 10/973,936, now U.S. Pat. No. 7,578,821, entitled "Dynamic Knee Balancer with Pressure Sensing"; 61/090,535 entitled "Sensing Force During Partial and Total Knee Replacement Surgery"; and 61/107,973 entitled "Dynamic Knee Balancing for Revision Procedures", the entireties of which had been previously incorporated herein by reference.

Figure 9:
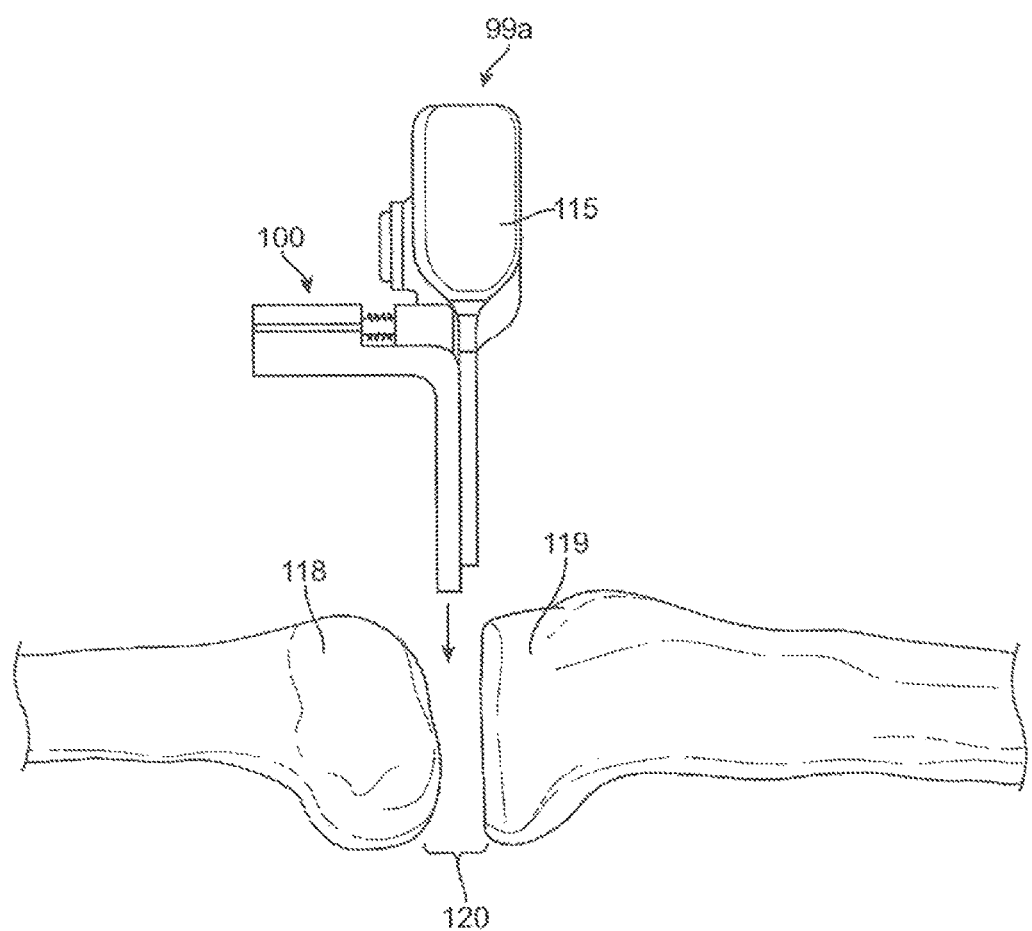
FIGS. 9-10 show a side view of a knee alignment system, including the distal femoral alignment component and the force sensor coupled together, being placed in the gap.
Figure 10:
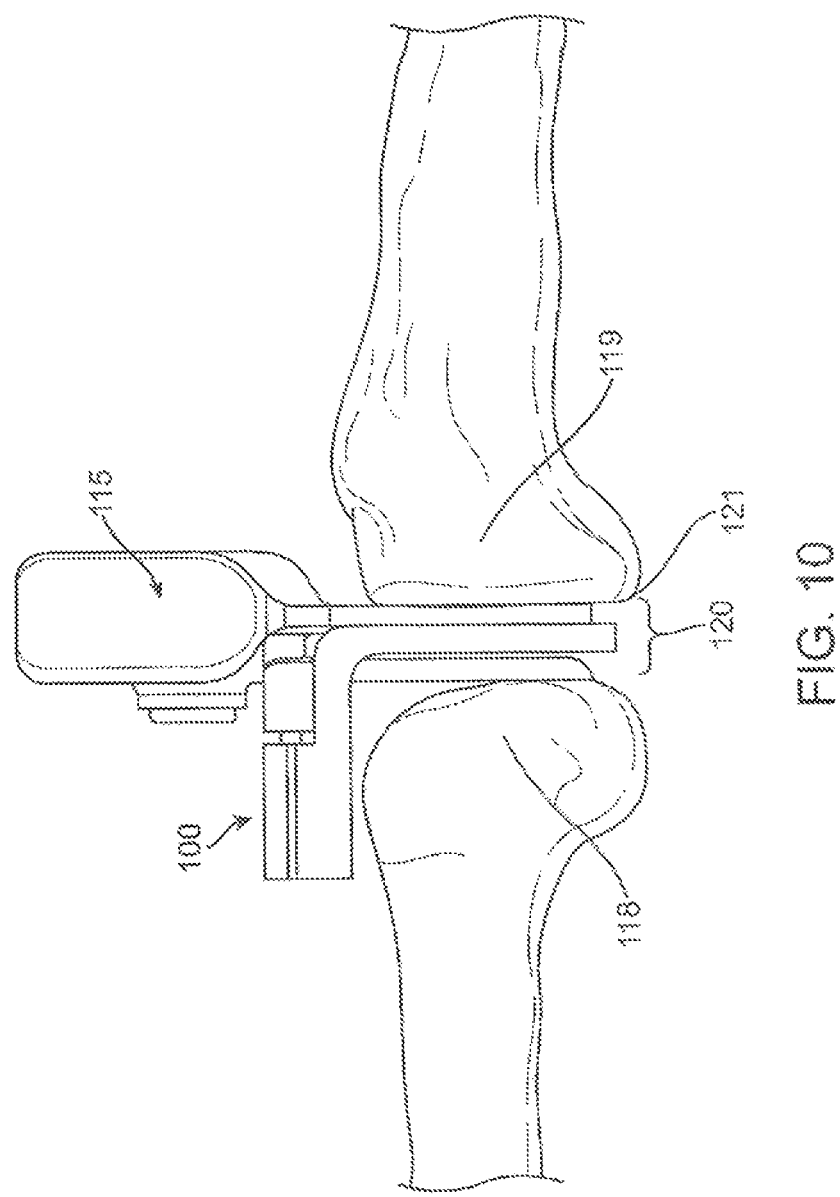
Figure 11:
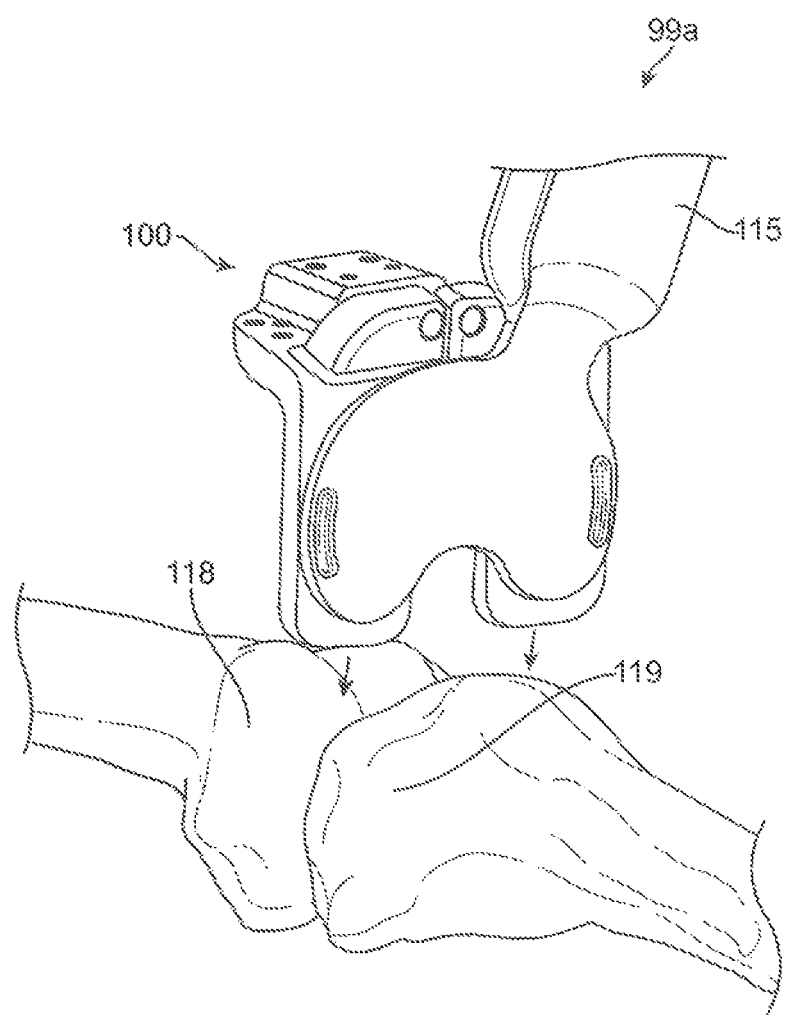
FIGS. 11-12 show a perspective view of a knee alignment system, including the distal femoral alignment component and the force sensor coupled together, being placed in the gap.
Figure 12:
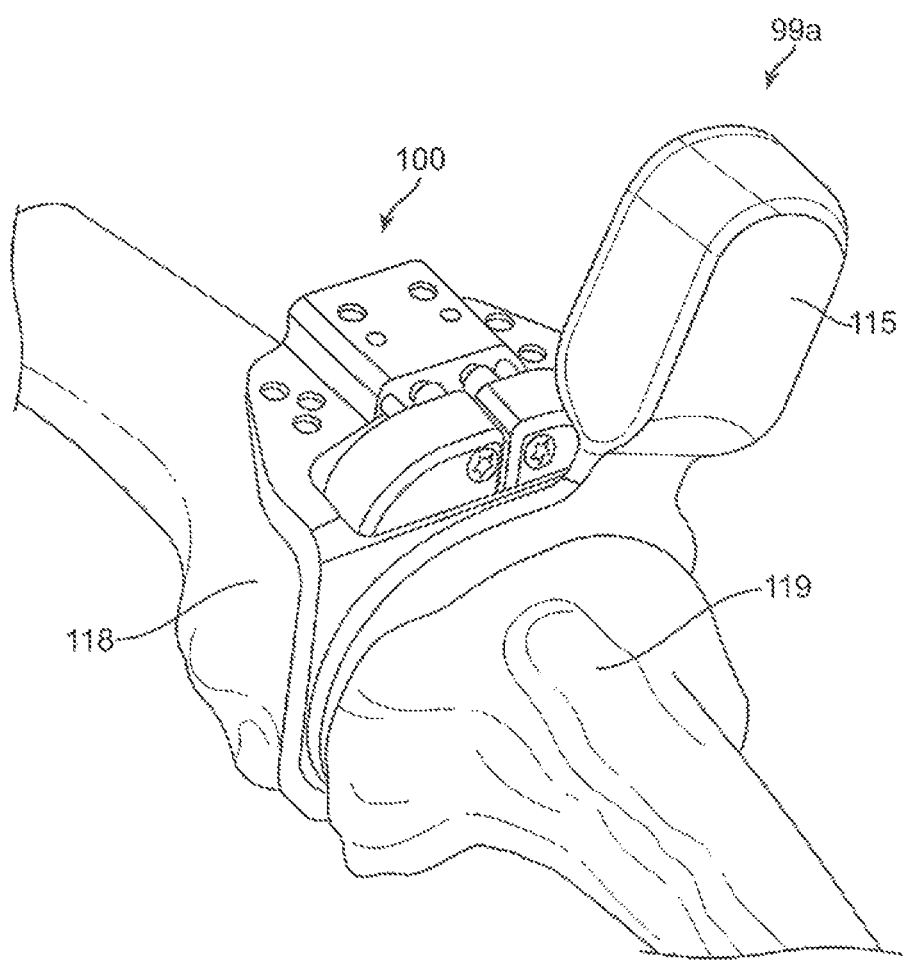
Figure 13:
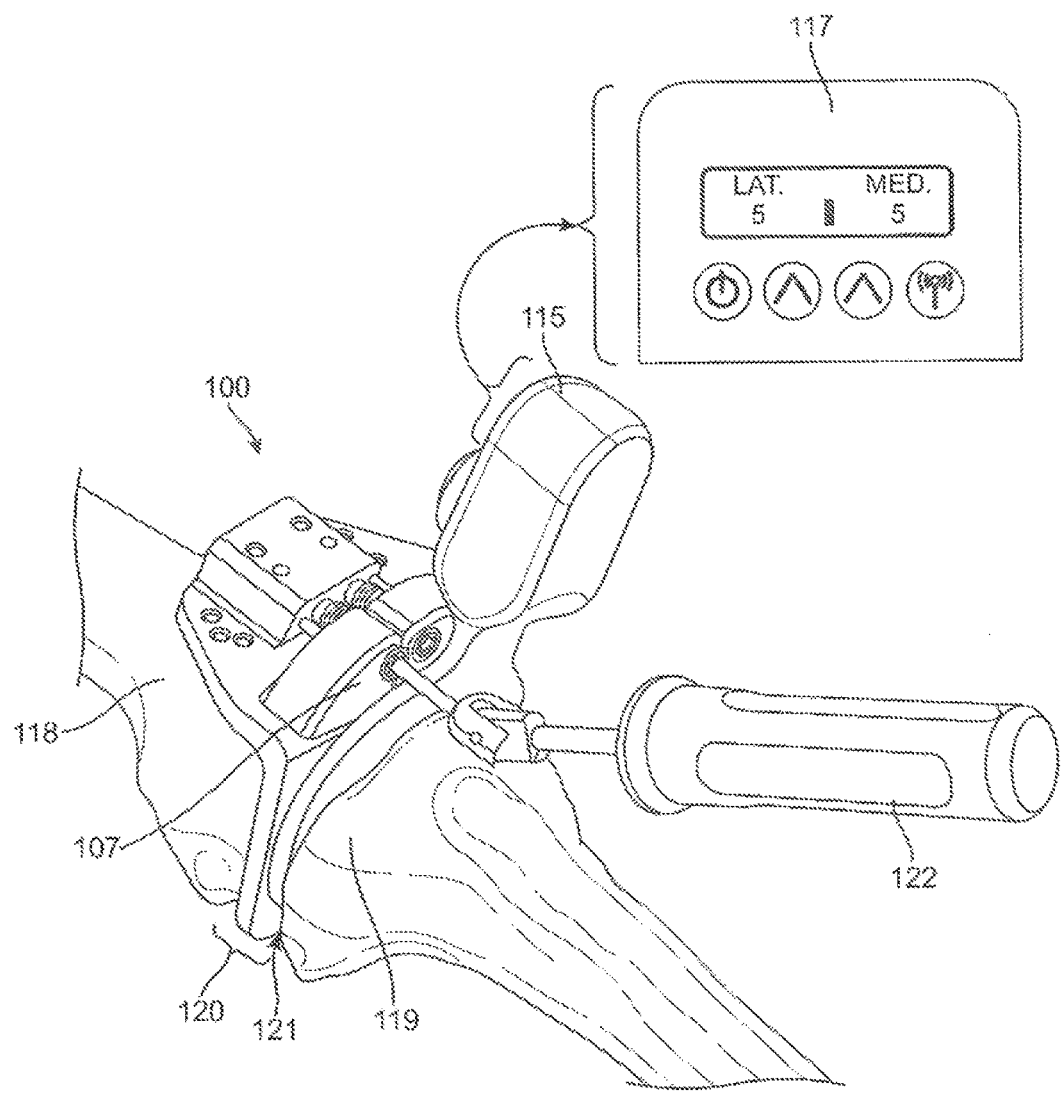
FIGS. 13-23 show a method of aligning a knee during surgery according to embodiments, of the invention.
Figure 14:
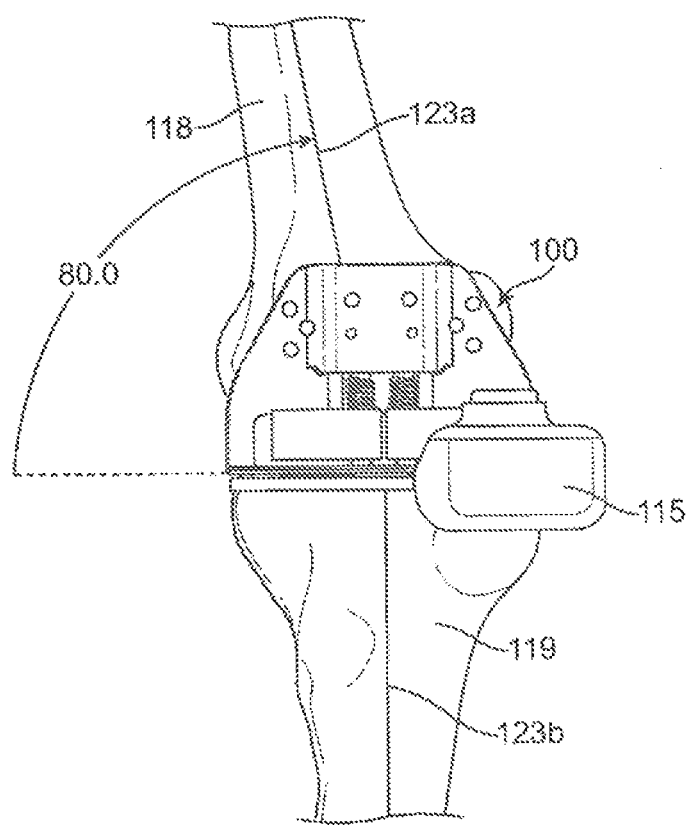
Figure 15:
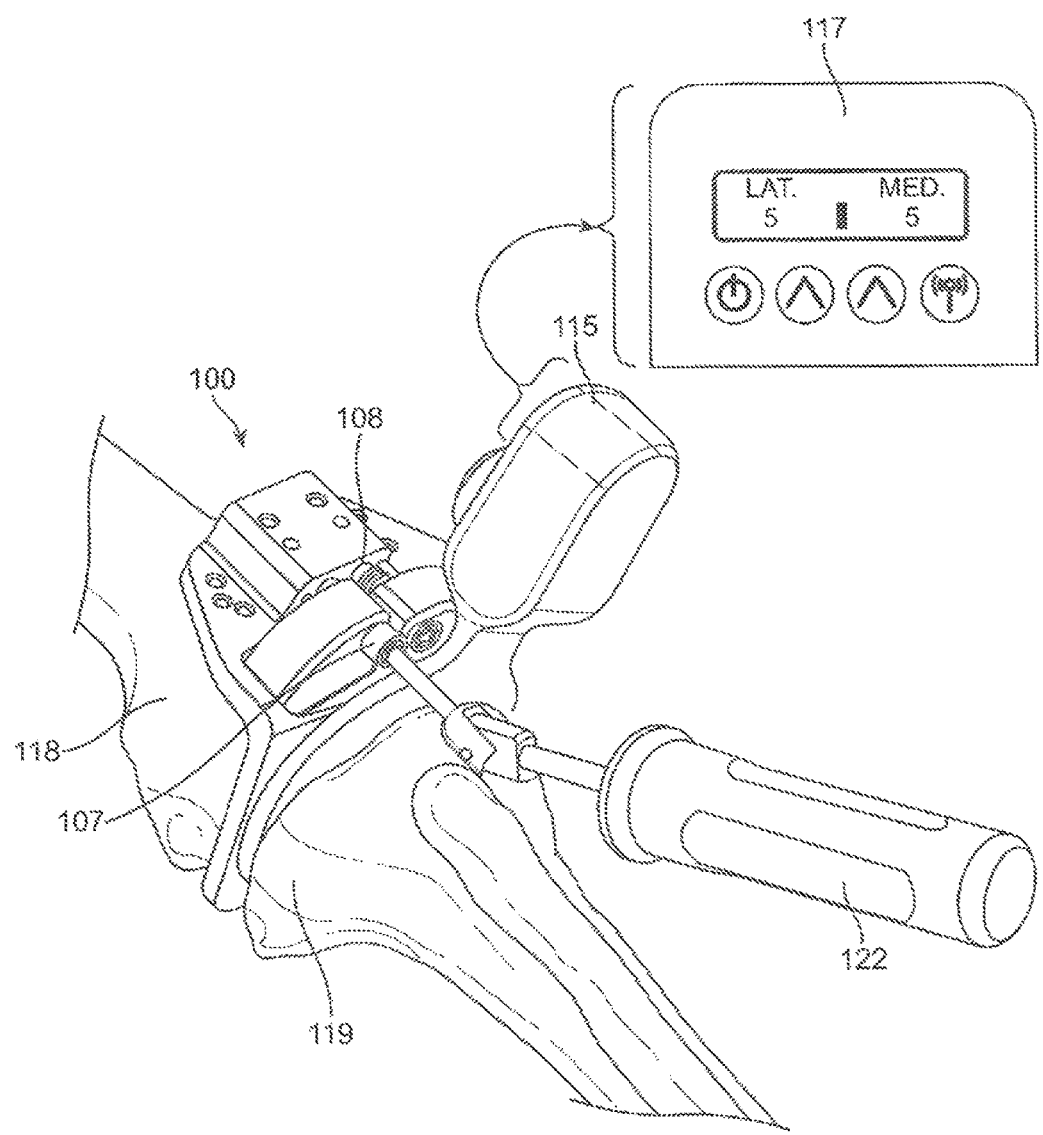
Figure 16:
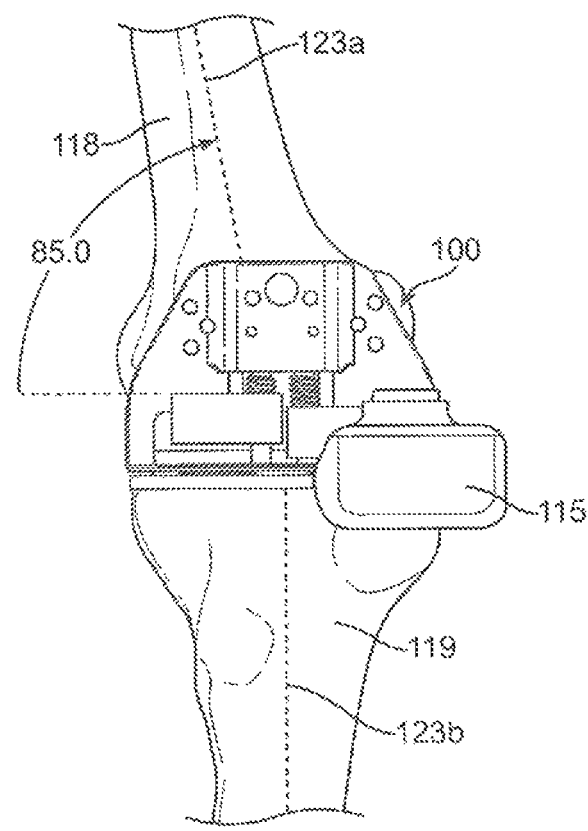

FIGS. 9-23 show a method of using an exemplary knee alignment system during knee replacement surgery according to embodiments of the invention. As shown in FIGS. 9 and 11, the force sensor 115 is coupled to the distal, femoral alignment assembly 100. As shown in FIGS. 10 and 12, the distal femoral alignment assembly 100 and the coupled force sensor 115 are placed in the gap 120 between the distal femur 118 and the tibial plateau 121 of the knee. As shown in FIG. 13, the force sensor 115 senses the forces between the lateral and medial portions of the distal femur and the tibial plateau. The visual display 117 shows the sensed forces (as an example, the display shows the forces unbalanced). An adjustment wrench 122 is coupled to rotatable distraction screw 107 of the distal femoral alignment assembly 100. As shown in FIG. 14, when the unadjusted distal femoral alignment assembly 100 and the coupled force sensor 115 are first placed in the gap 120 between the distal femur 118 and the tibial plateau 121, the knee may be misaligned, i.e., the femoral axis and the tibial axis are not aligned with each other as in a normal knee. As shown in FIG. 14, the bottom surface of the distal femoral alignment assembly is 80° relative to the mechanical axis 123 of the femur 118. As shown in FIG. 15, at least one of the rotatable screws 107, 108 is rotated with the adjustment wench 122 to adjust the relative position of the adjustable medial and/or femoral portions and to correct the alignment of the knee. Generally, by balancing the sensed forces in the medial and lateral portions of the knee, correct alignment of the knee can be achieved (as shown in the visual display). For example, as shown in FIG. 16, the distal, femoral alignment assembly 100 has been adjusted so that the bottom surface of the distal femoral alignment assembly is 85° relative to the mechanical axis 123 of the femur 118.

Figure 17:
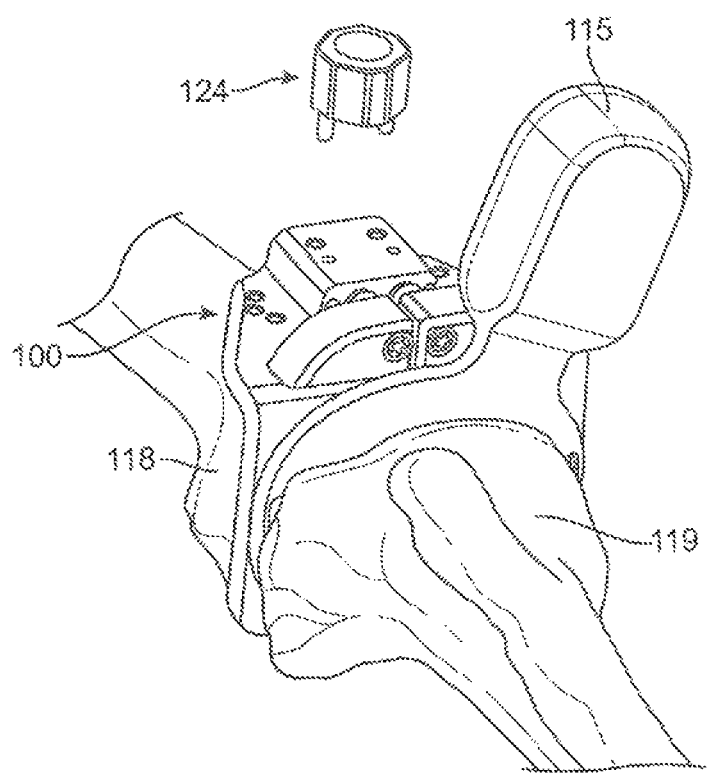
Figure 18:
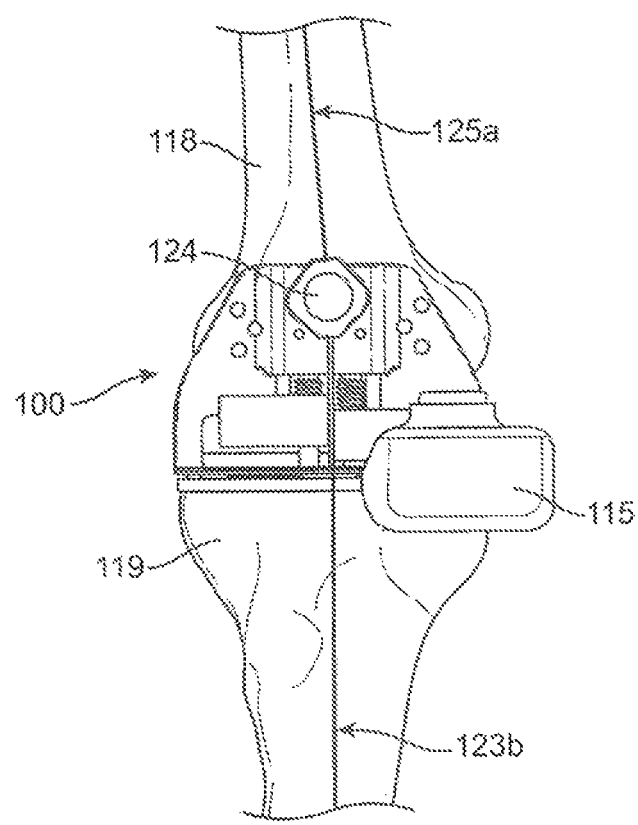
Figure 19:
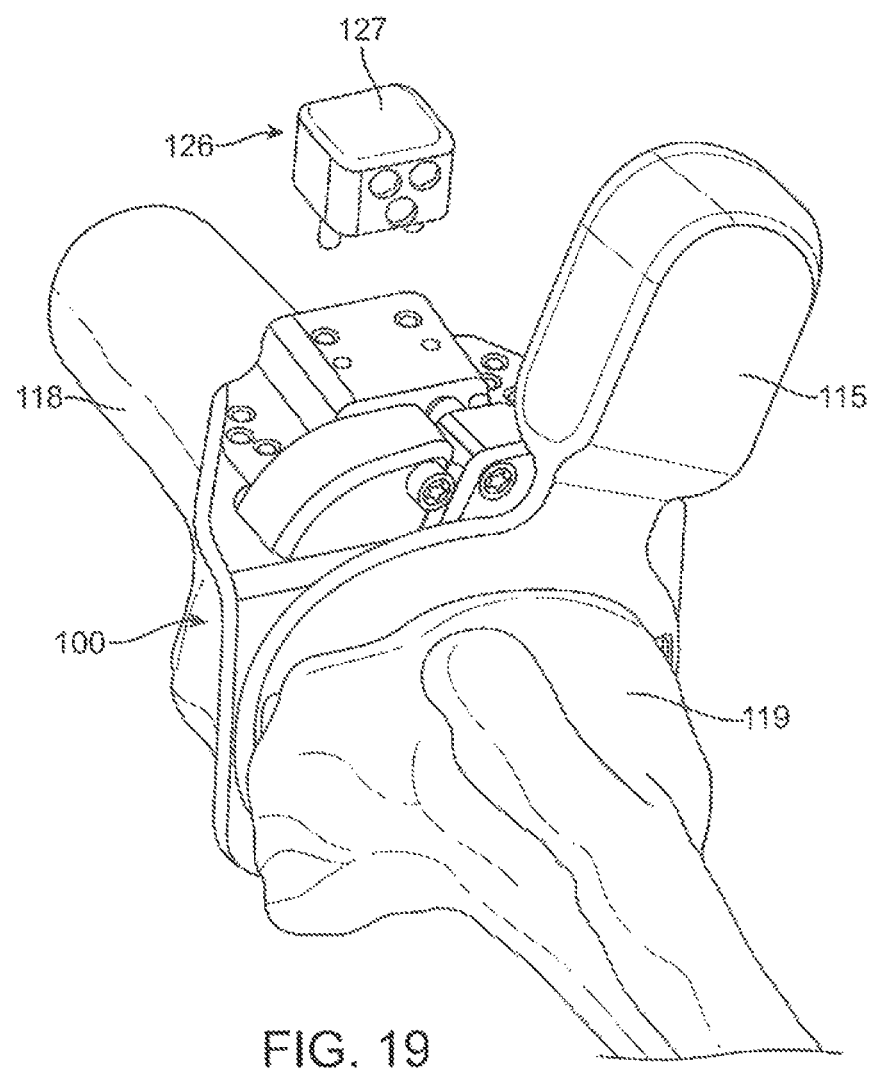
Figure 20:
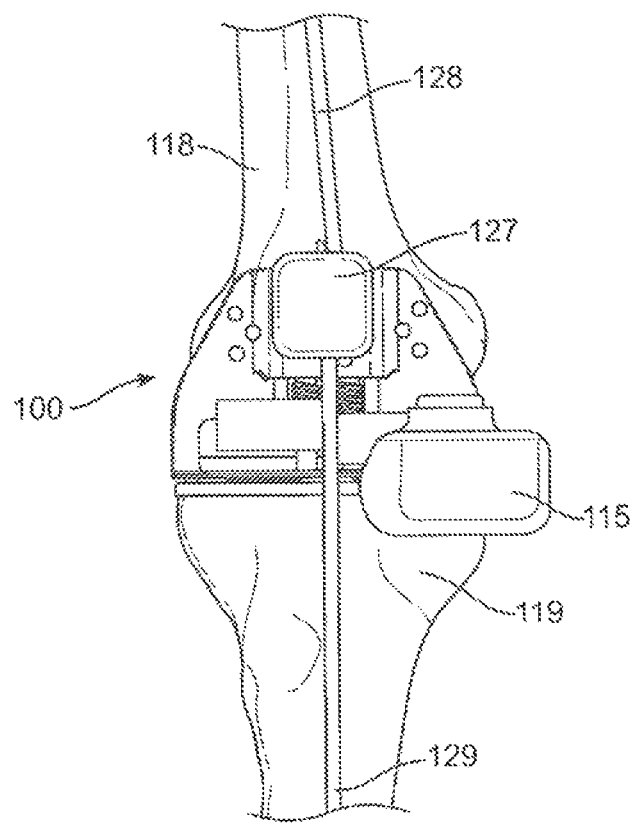

The system, will typically former comprise a knee alignment verification means to verify the alignment of the knee by verifying the angle formed by the mechanical axes of the femur and tibia. As shown in FIGS. 17 and 18, the knee alignment verification means may be a laser knee, alignment verification member 124 coupleable to the main body of the distal femoral alignment member 100. As shown in FIG. 18, the laser knee alignment verification member 124 emits a femoral laser beam 125a to be aligned along the mechanical axis 123a of the femur and a tibial laser beam 125b to be aligned along the mechanical axis 123b of the tibia. The angle of the femoral laser beam and the tibial laser beam relative to each other can be used by the surgeon to verily the proper anatomical alignment of the knee, i.e., the angle between the mechanical axes 123a, 123b of the femur and tibia. Alternatively, as shown in FIGS. 19 and 20, the knee alignment verification means may be a mechanical knee alignment verification assembly 126. The mechanical knee alignment verification assembly 126 comprises a mechanical, knee alignment verification huh 127, a femoral alignment rod 128 coupleable with the hub 127, and a tibial alignment rod 129 coupleable with the hub 127. The coupled femoral alignment, rod 127 can be aligned along the mechanical axis 123a of the femur 118. The coupled tibial alignment rod 129 can be aligned along the mechanical axis 123b of the tibia 119. The angle of the femoral alignment rod 128 and the tibial alignment rod 129 relative to each other can be used by the surgeon to verify proper alignment of the knee.

Figure 21:
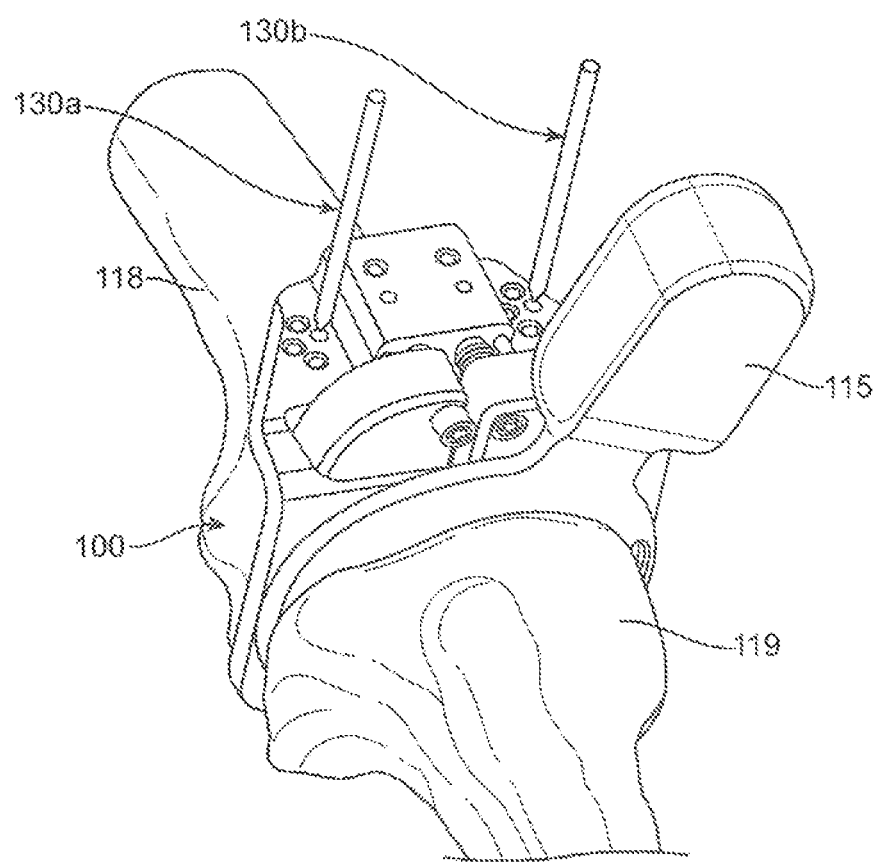
Figure 22:
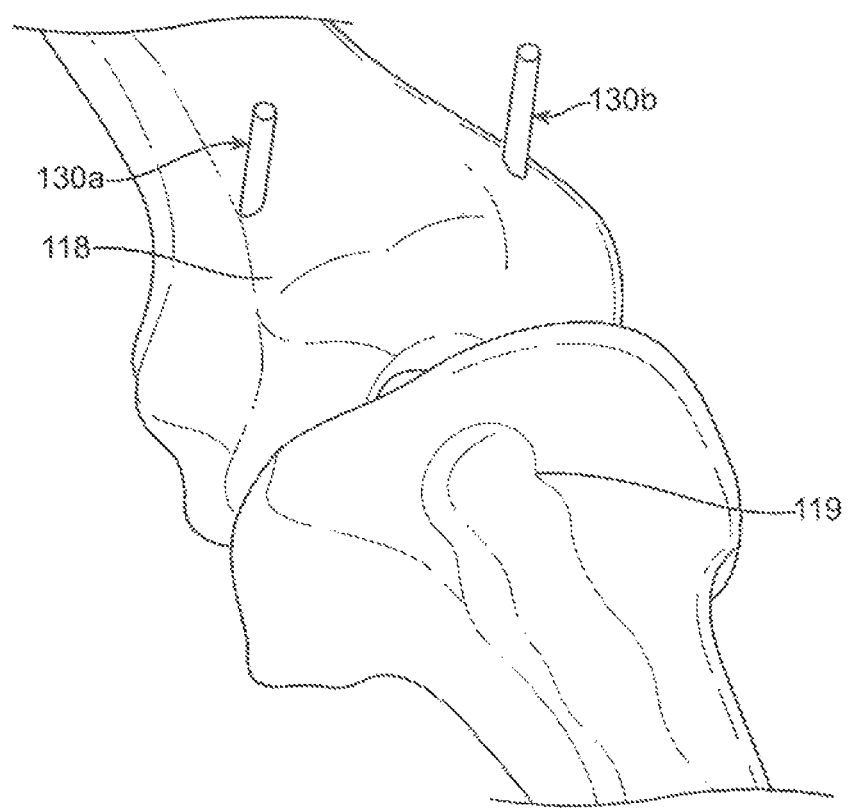

As shown in FIG. 21, the system may further comprise a plurality of locating pins 130a, 130b. When the knee is properly aligned, at least one locating pin (130a and/or 130b) may be placed on the medial side of the distal femur 118 and at least one locating pin may be placed on the lateral side of the distal femur as guided by the apertures of the distal femoral alignment assembly. As shown in FIG. 22, once the locating pins 130a, 130b are placed on the distal femur 118, the distal femoral alignment assembly 100 may be disengaged from the distal femur.

Figure 23:
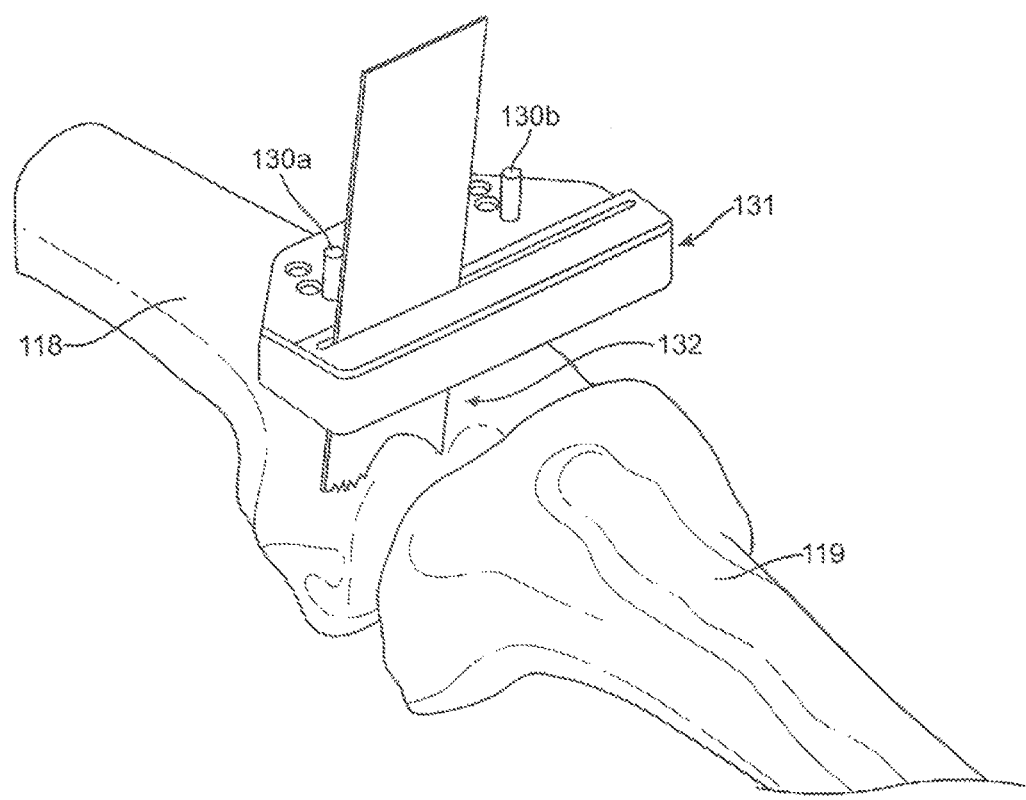

As shown, in FIG. 23, the system may further comprise a distal femoral cutting guide 131 which can be coupled to the distal femur 118 and positioned based on the position of the locating pins 130a, 130b. Cuts are made on the distal femur 118, for example, with a surgical saw blades 132. Typically, these cuts will form the basis for positioning of the femoral portion of an artificial knee. Exemplary surgical saw blades which may be used to make these cuts on the distal femur are described co-assigned U.S. Pat. Nos. 6,022,353; 6,503,253; and 6,723,101, the entire contents of which are incorporated herein by reference.

Figure 25:
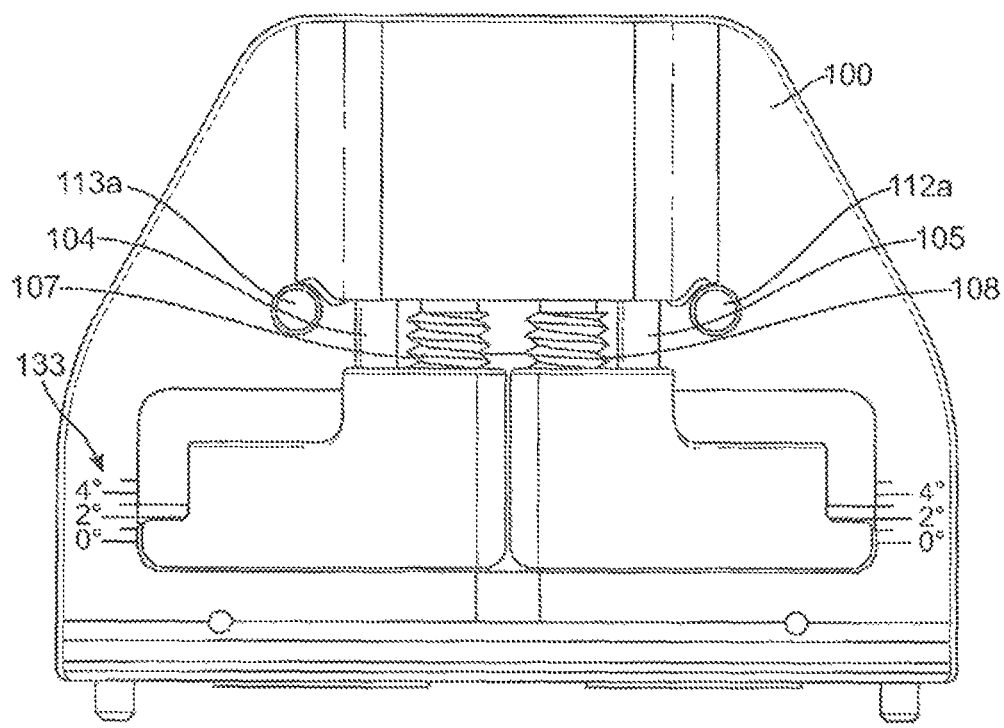
FIG. 25 shows a top view of the unadjusted distal femoral alignment assembly.
Figure 26:
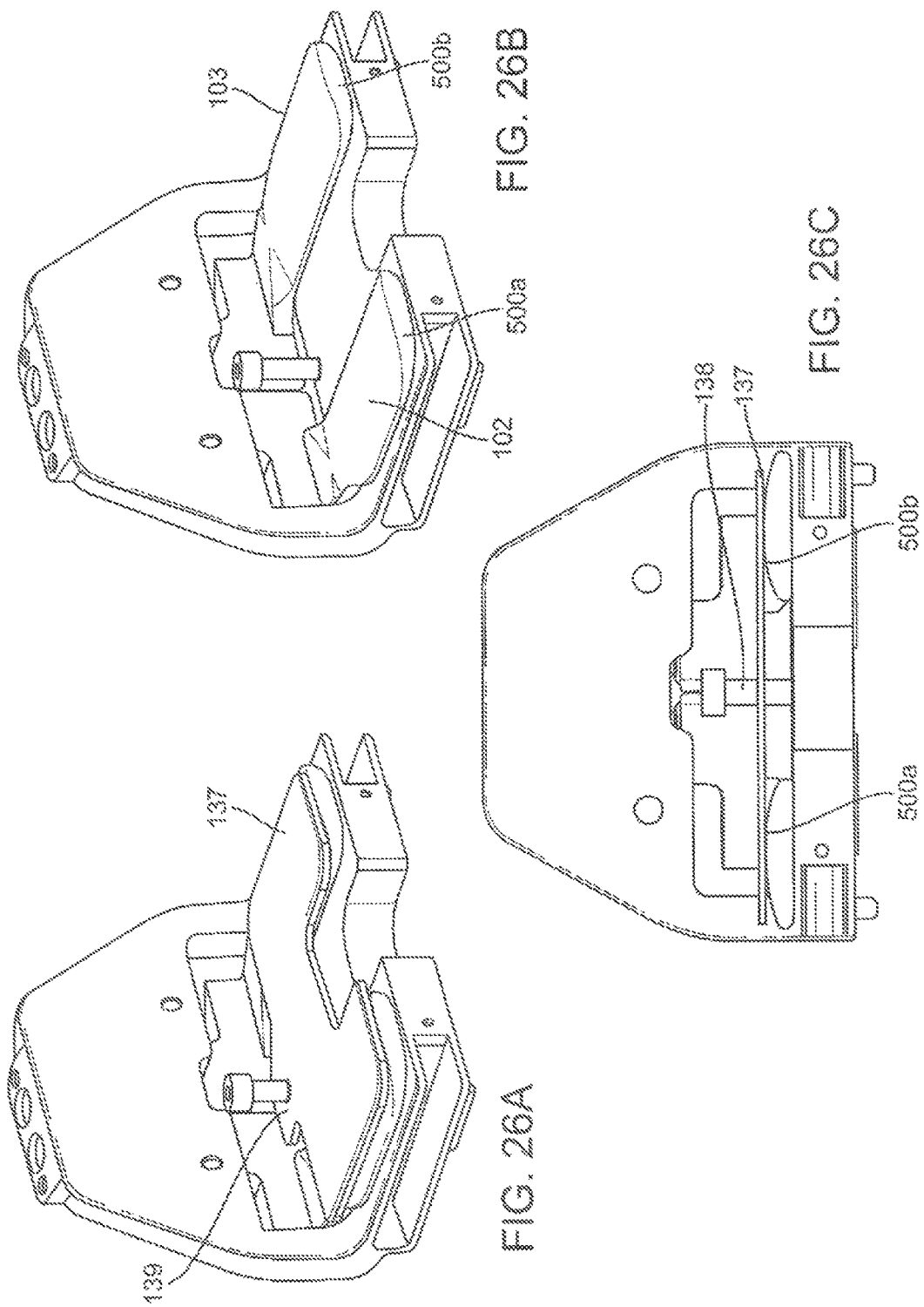
FIGS. 26A and 26C show perspective posterior views of the unadjusted distal femoral alignment assembly shown in FIG. 25.
FIG. 26B shows a posterior perspective of the unadjusted distal femoral alignment assemblies shown in FIGS. 26A and 26C with the bone interface plate removed.
Figure 27:
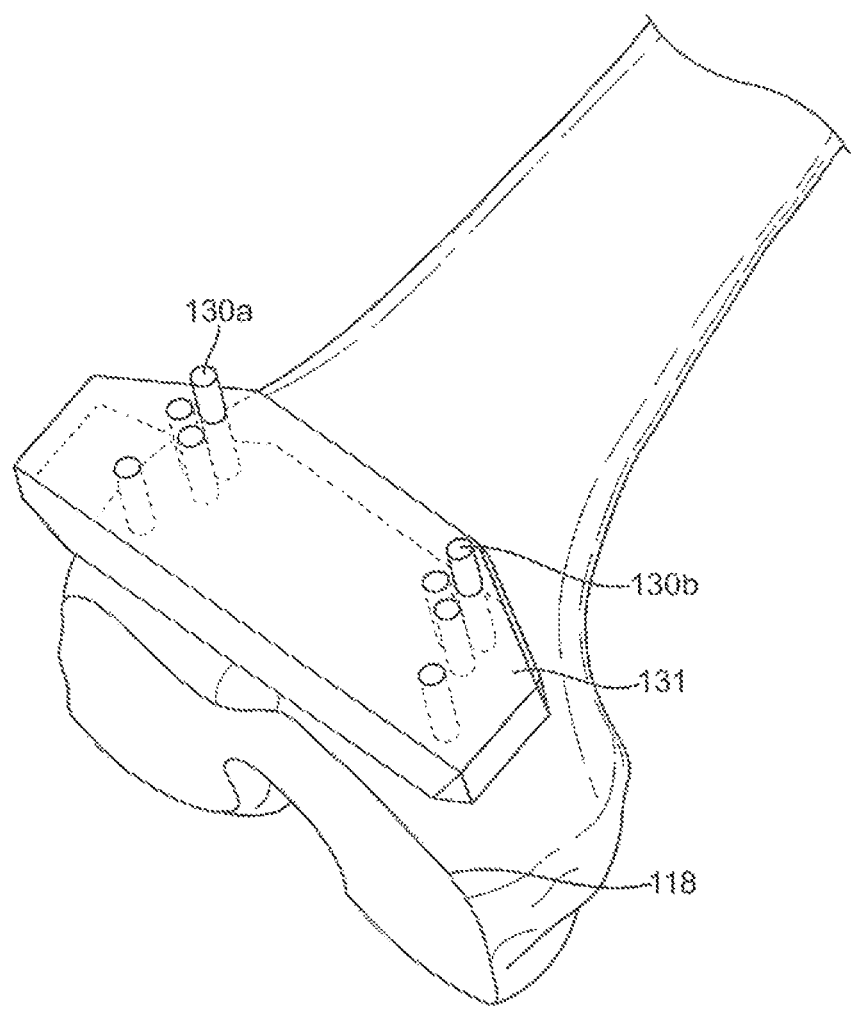
FIGS. 27-33 show an alternative method of aligning a knee surgery according to embodiments of the invention.
Figure 28:
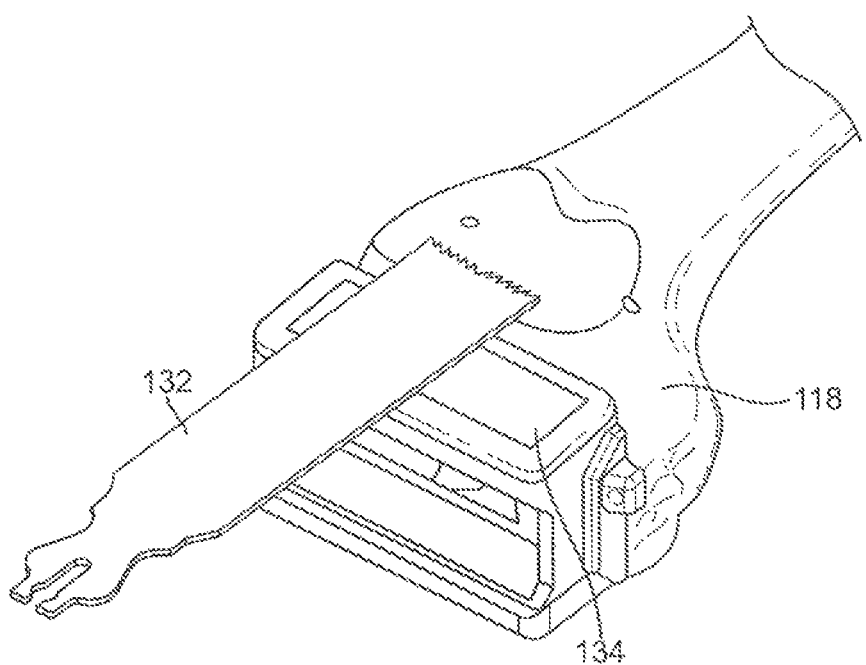
Figure 29:
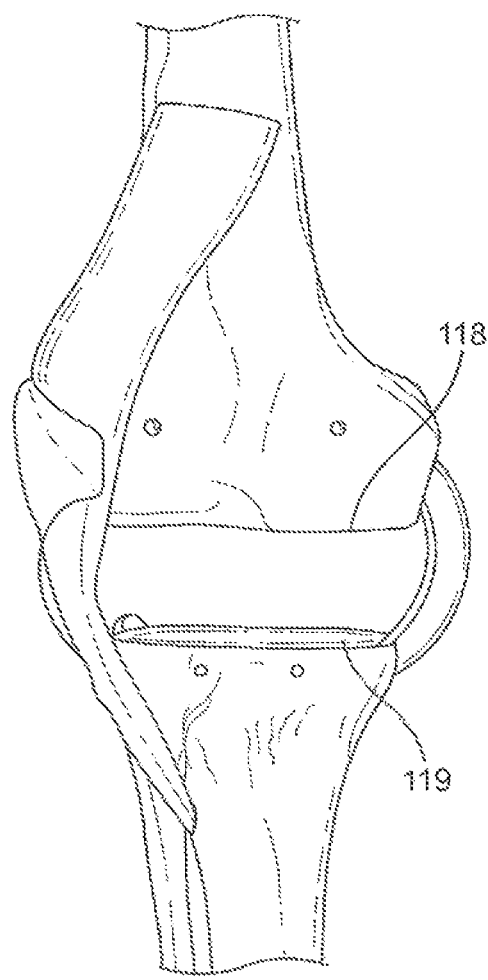

Referring now to FIGS. 24A-B, an alternative distal femoral alignment system 99b is shown including cutting guide 131 for making a provisional cut on the distal femur in order to mount the distal femoral alignment, assembly 100 flush against the provisionally cut distal femur. As shown in FIG. 25, angular graduation marks 133 are provided. The graduation marks correspond to movement created by adjusting either the medial or lateral distraction paddles 102, 103 as shown in FIG. 26B. For clarity purposes, a right distal femur is shown in FIGS. 27-28 and 34-35 and a right knee joint with femur and tibia is shown in FIGS. 29-33. The medial side of components or assemblies of the distal femoral alignment system shown in FIG. 24 are hereby described either medial or lateral based on their position when used on a right knee. Of course, the invention can be used on the left and/or right knees. Convex shaped pivot fulcrums 500a, 500b are provided on the surfaces of the distraction paddles 102, 103 which directly contact the provisionally cut distal femur when the distal femoral alignment assembly 100 is mounted against the distal femur 118. The curved, surface of the distraction paddles 102, 103 creates fixed distance fulcrum points to determine how much angle is being adjusted. FIGS. 26A and 26C show another embodiment of the distal femoral alignment assembly 100 of the alternative distal femoral alignment system 99b shown in FIG. 24, which includes bone interface plate 137. This plate 137 provides protection from convex shaped distraction paddles 102 and 103 from indenting the softer cancellous bone exposed as a result of a provisional cut being made oft the distal femur 118 (not shown in FIG. 26). FIG. 26C shows the bone interface plate 137 sitting on top of convex shaped distraction paddles 102 and 103 in their unadjusted position. Shoulder screw 138 is shown, which slips through a loosely fitted hole 139 in bone interface plate 137 to allow for tilting of bone interlace plate 137 when convex shaped distraction paddles 102 and 103 are adjusted from their unadjusted position to an adjusted position. Spacing between convex shaped adjustment paddies 102 and 103 is maintained in the medial-lateral direction, to provide for a known pivot fulcrum between the two convex shaped adjustment paddles, which corresponds to angular graduations 133 shown in FIG. 25. The angular gradations provide an indication of the angle between the femur and tibia Referring now to FIGS. 27-35, a method of using an exemplary knee alignment system used during knee replacement surgery is shown according to embodiments of the invention. For purposes of clarity, a bone cat has already been made on the proximal tibia 119 prior to the methods described in FIGS. 27-35. FIG. 27 shows provisional distal femoral cutting guide 131 moveably attached to the provisionally cut distal femur 118 via two pins 130a and 130b. FIG. 28 shows provisional femoral cutting guide 131 and pins 130a and 130b now having been removed and femoral anterior-posterior cutting guide 134 is now removably attached to distal femur 118. Saw blade 132 is shown and the anterior and posterior bone cuts are performed on distal femur 118. FIG. 29 shows now the "extension gap" with the proximal tibial cut having been made and a provisional distal femoral cut having been made. The posterior femoral cut has also been made but hidden from view in FIG. 29. The anterior cut has also been made on distal femur 118.

Figure 30:
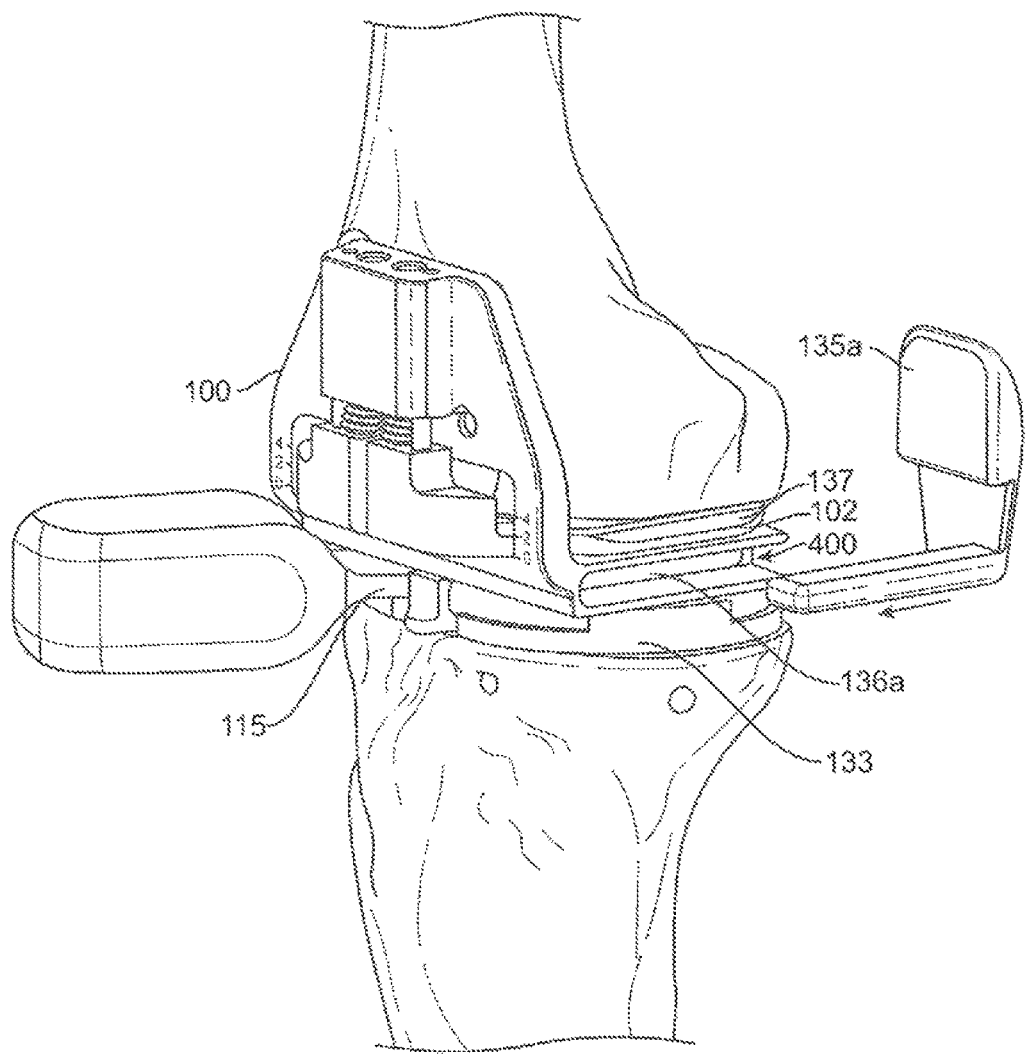
Figure 31:
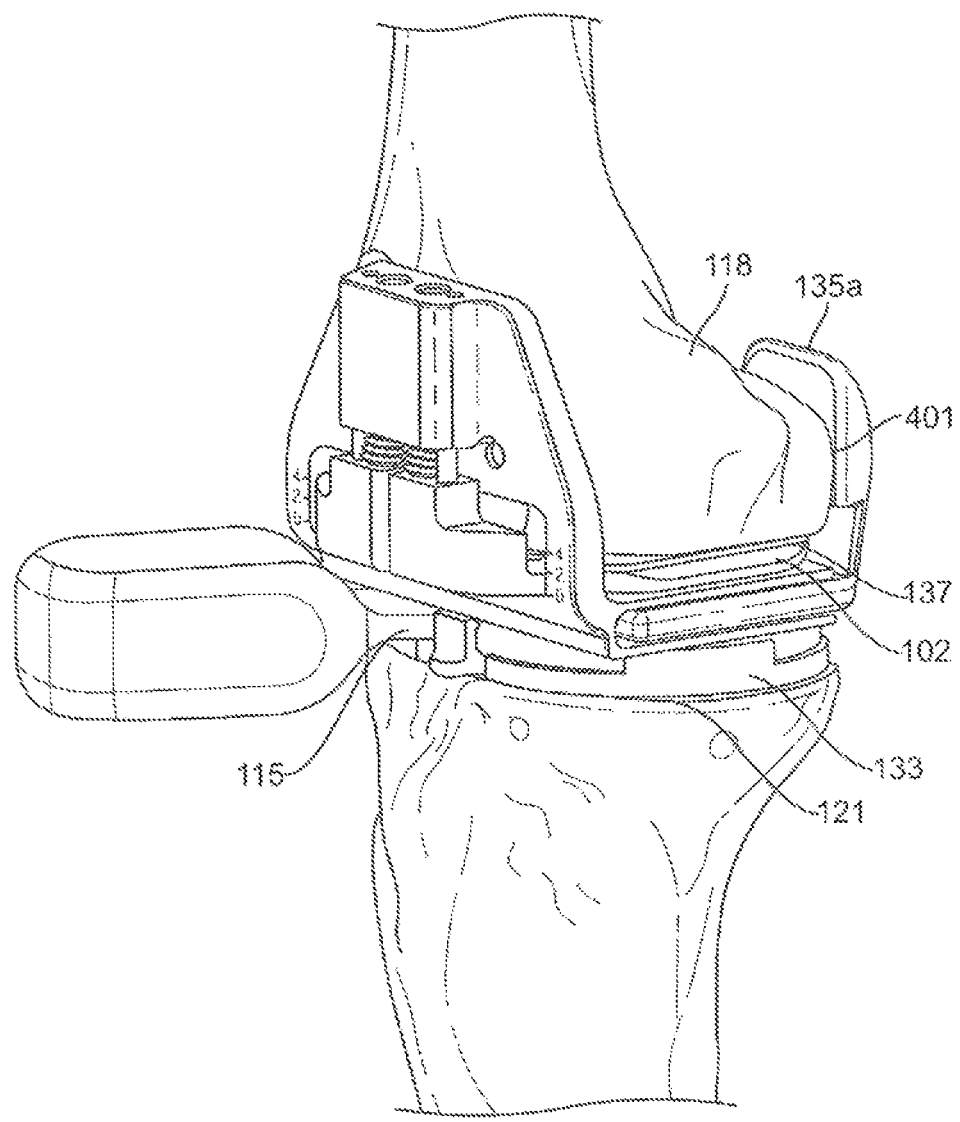
Figure 32:
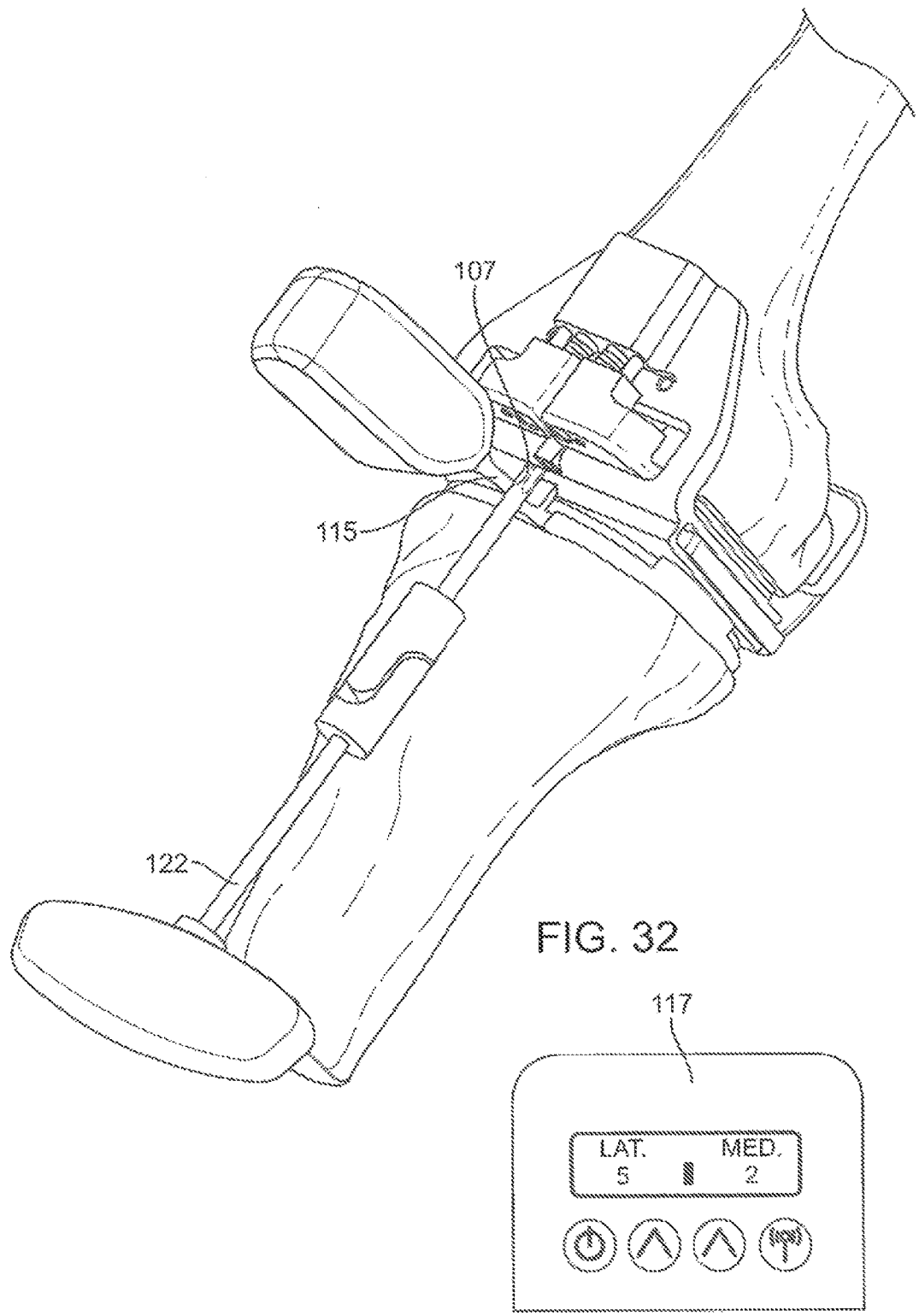
Figure 33:
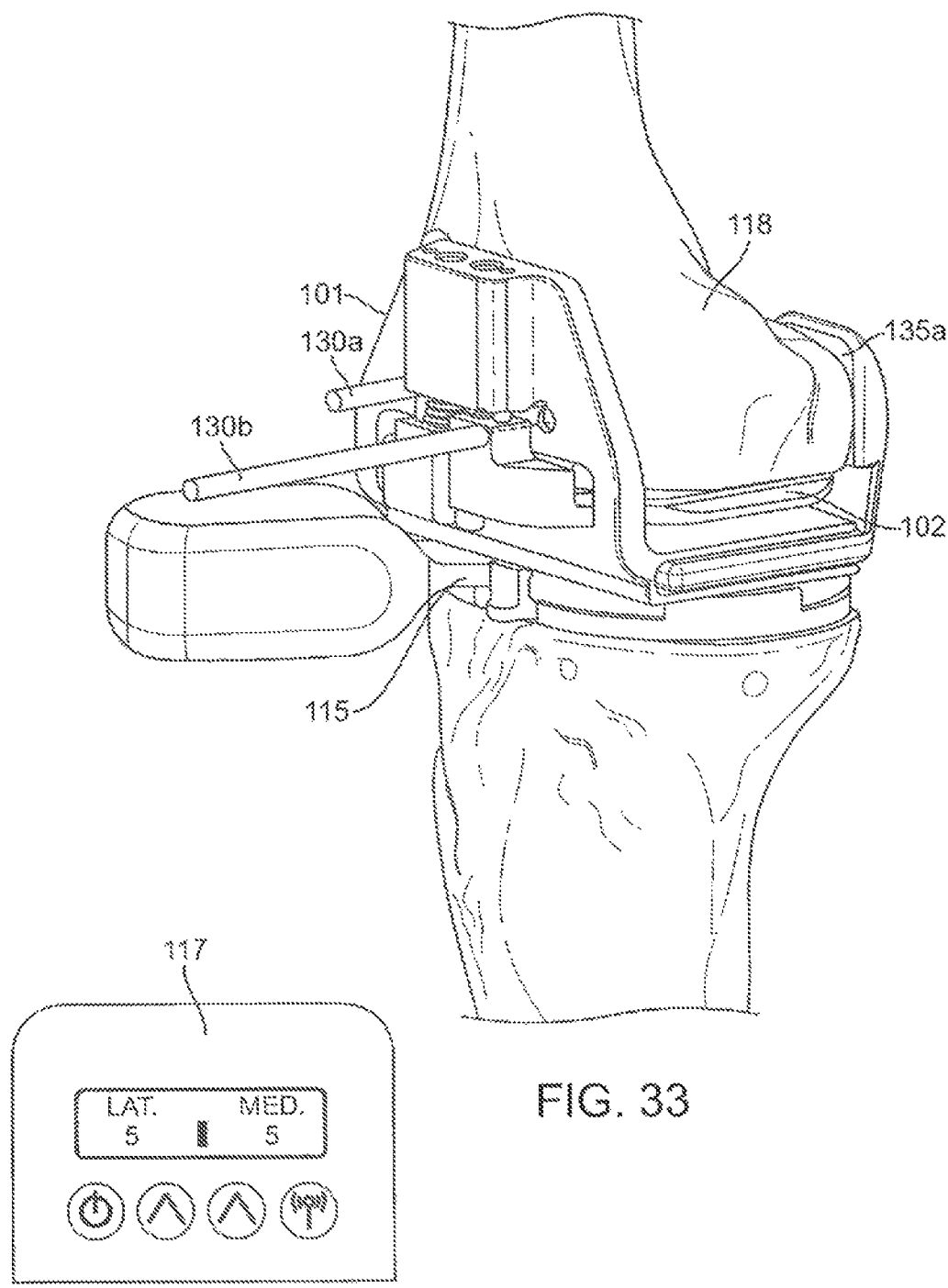
Figure 34B:
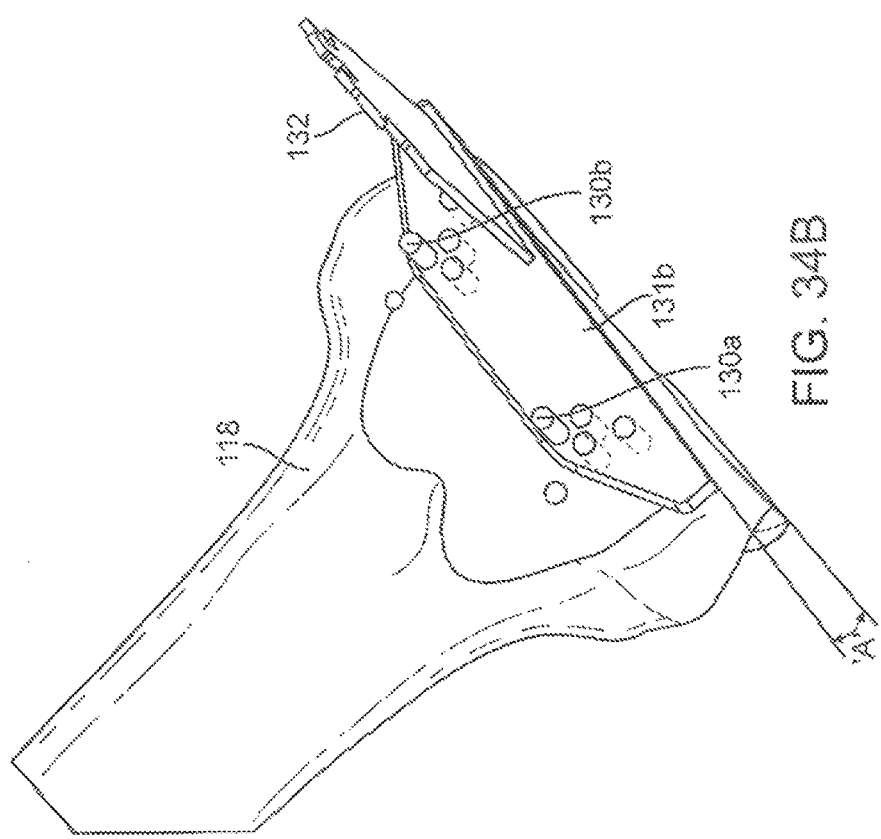
Figure 34A:
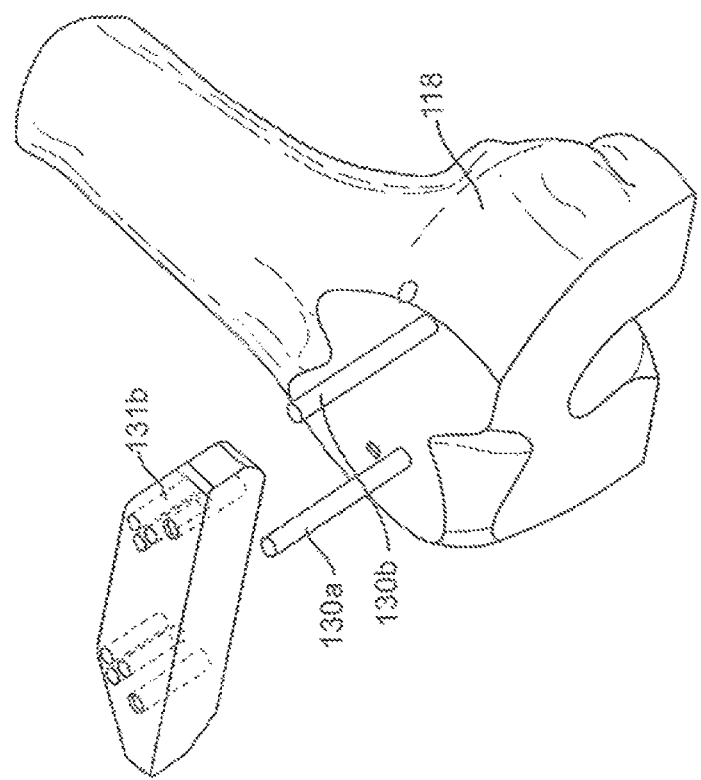
Figure 35:
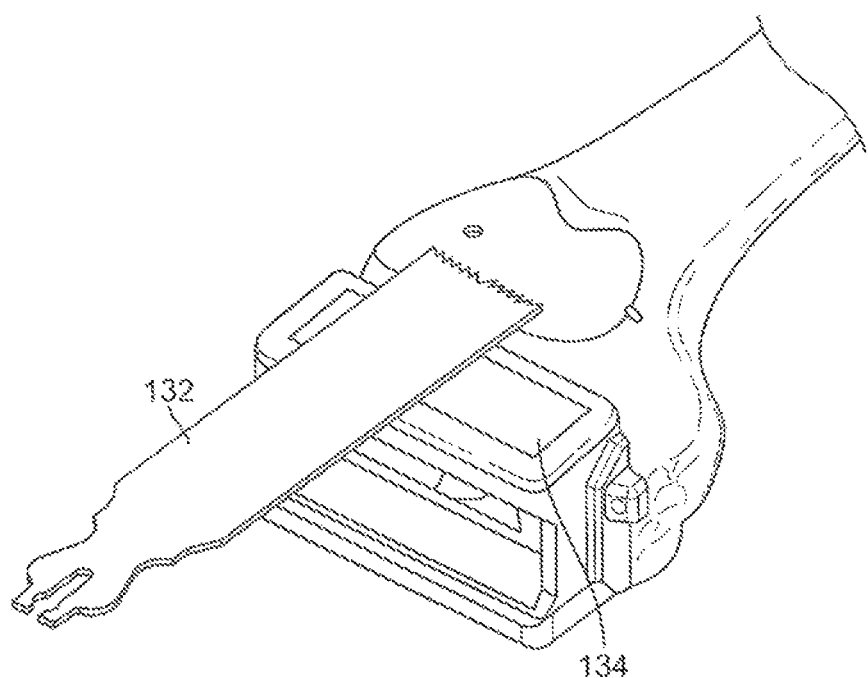
Figure 36:
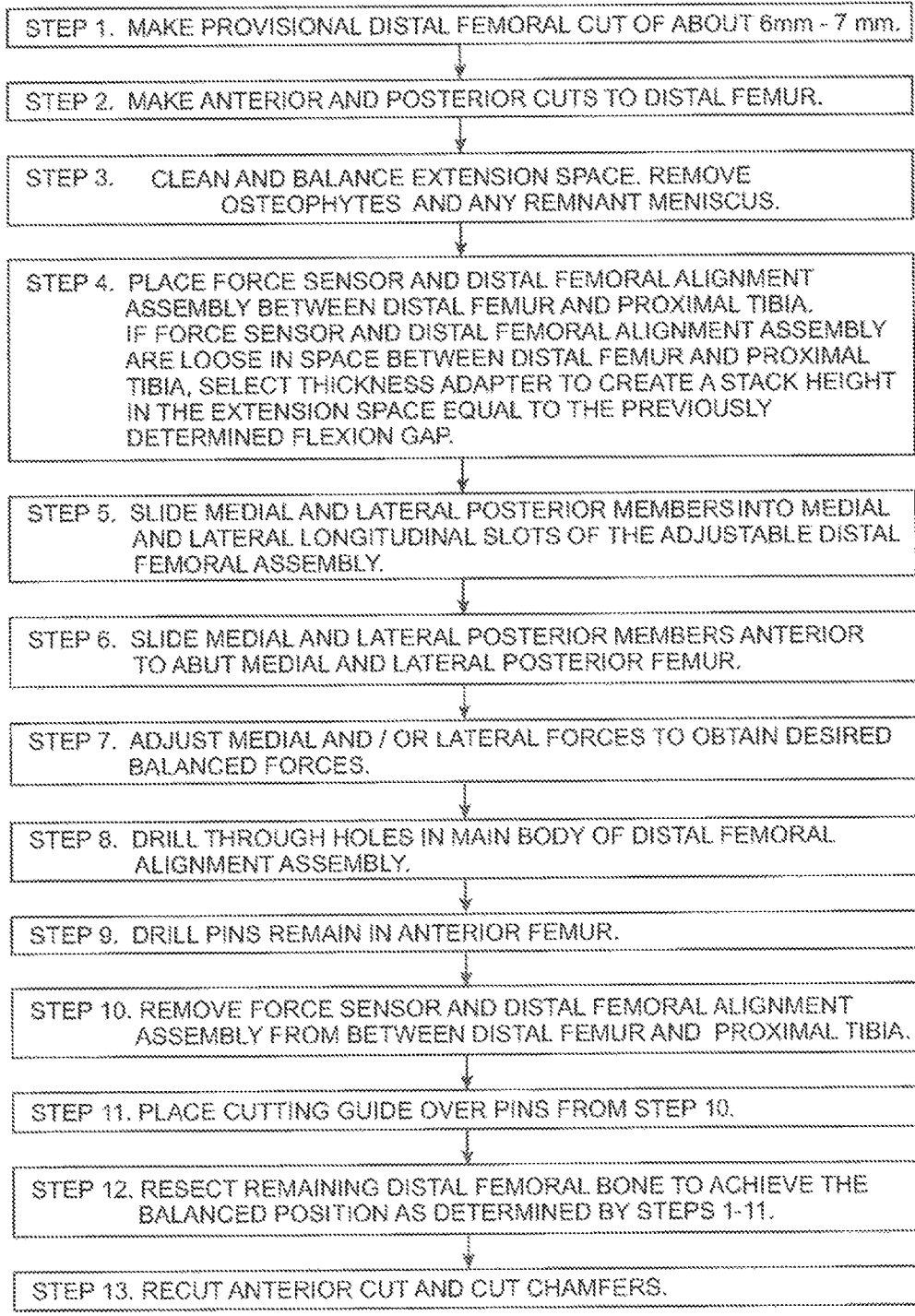
FIG. 36 is a flow chart schematically illustrating a method for aligning and balancing a knee during knee surgery according to embodiments of the invention.

Moving now to FIG. 30, the distal femoral alignment assembly 100 and other components of the distal femoral alignment system 99b are shown between the proximal tibia 119 and the distal lemur 118, with the leg in fell extension. Thickness adapter 133 is shown moveably coupled to force sensor 115, and force sensor 115 is moveable coupled to distal femoral assembly 100. Adjustable posterior member 135a is shown adjacent to a longitudinal slot 400 open on the posterior side of distal femoral assembly 100, with the slot closed on the anterior side of the distal femoral assembly 100. FIG. 31 shows-adjustable posterior member 135a having now been moveably coupled within the longitudinal slot 400 along the medial side of distal femoral assembly 100. Moveable coupling means 136a, 136b can include magnets or other common coupling means such as screws or spring clips. Longitudinal slots are also provided on the opposite side of the distal femoral assembly 100. Longitudinal slots along the sides of distal femoral, assembly 100 are of adequate length to allow for anterior-posterior adjustment of adjustable posterior member to abut the previously made posterior cut 401 of the distal femur 118. The adjustable posterior members further balance extension filling the posterior space with a condylar thickness similar to the posterior condylar thickness of the femoral component to be implanted thus taking into account soft-tissue tendencies, or bias. FIG. 32 shows components and assemblies of the distal femoral alignment system 99b now completely in place between the proximal tibia and the distal femur and force readings coupled from force sensor 115 are being displayed on display 117, it is understood that display 117 may be integral to force sensor 115. The display 117 can also be separable from the sensor. The display 117 is showing force readings of 5 and 2 lateral and medial respectively, indicating lower force between the medial side of the distal femur and the medial side of the proximal tibia, in this example. Adjustment wrench 122 is shown in line with the medial distraction screw 107. FIG. 33 shows the medial distraction paddle 102 having now been adjusted to a point wherein the forces being measured by sensor 115 and displayed by display 117 read 5 on both the lateral and the medial side. Pin 130a is shown being driven through a lateral side cutting guide beating aperture and pin 130b has yet to be driven through the medial side cutting guide locating aperture. FIG. 34A shows both pins having now been driven through cutting guide locating apertures of distal femoral assembly 100, and distal femoral assembly 100 now having been removed from the distal femur 118. Cutting-guide 131b is positioned over pins 130a and 130b. FIG. 34B shows cutting guide 131b now positioned over pins 130a and 130b and saw blade 132 will be used to make the final distal femoral cat at an angle "A" which, is the plane of balanced resection as determined by the force sensor. FIG. 35 shows femoral anterior-posterior cutting guide 134 now removably coupled to distal femur 118 and saw blade 132 is shown making a final cut on the anterior distal femur. Anterior and posterior chamfer cuts will also be made on the distal femur 118 at this point.

While the above is a complete description of the preferred embodiments of the invention, various alternatives, modifications, and equivalents may be used. Therefore, the above description should not be taken as limiting in scope of the invention which is defined by the appended claims.

What is claimed is:

1. A femoral cut guide alignment assembly removably engagable with a distal end of a femur, the femoral cut guide alignment assembly comprising:
   a stationary femoral portion including angular graduations indicative of an angle between the femur and a tibia;
   an adjustable medial femoral portion coupled to the stationary femoral portion, the adjustable medial femoral portion including a medial paddle, an anti-rotation shaft, and a distraction screw, the medial paddle including a proximal convex shaped surface; and
   an adjustable lateral femoral portion coupled to the stationary femoral portion, the adjustable lateral femoral portion including a medial paddle, an anti-rotation shaft, and a distraction screw, the lateral paddle including a proximal convex shaped surface,
   wherein a spacing between the adjustable medial femoral portion and the adjustable lateral femoral portion is maintained to provide a known pivot fulcrum between the femoral portions that corresponds to the angular graduations on the stationary femoral portion; and
   wherein the proximal convex shaped surfaces create respectively a medial pivot fulcrum and a lateral pivot fulcrum within the femoral assembly.

2. The femoral cut guide alignment assembly of claim 1, further comprising a bone interface plate spanning the medial pivot fulcrum and the lateral pivot fulcrum.

3. The femoral cut guide alignment assembly of claim 1, further comprising a bone interface plate spanning the adjustable medial femoral portion and the adjustable lateral femoral portion to provide protection to a provisionally cut distal femur.

4. The femoral cut guide alignment assembly of claim 3, further comprising a shoulder screw disposed between the adjustable medial femoral portion and the adjustable medial femoral portion and secured to the stationary femoral portion to assist in maintaining the known pivot fulcrum; and
wherein the bone interface plate includes a hole sized larger than the shoulder screw and positioned to accept passage of the shoulder screw when the shoulder screw is secured to the stationary femoral portion.

5. The femoral cut guide alignment assembly of claim 1, wherein the angular graduations indicative of an angle between the femur and a tibia are displayed on both a medial and a lateral side of the stationary femoral portion.

6. The femoral cut guide alignment assembly of claim 1, further comprising a knee alignment verification member coupleable with the stationary femoral portion of the femoral assembly to provide a concurrent visual confirmation of an angle of at least a portion of the femoral cut guide alignment assembly in reference to the femur and the tibia.

7. The femoral cut guide alignment assembly of claim 6, wherein the knee alignment verification member includes a laser knee alignment verification member providing a first laser beam oriented along the femoral axis of the knee and a second laser beam oriented along the tibial axis of the knee.

8. The femoral cut guide alignment assembly of claim 6, wherein the knee alignment verification member includes a mechanical knee alignment verification assembly, the mechanical knee alignment verification assembly comprising:
a knee alignment hub;
a first rod coupleable with the knee alignment hub to be oriented along the femoral axis of the knee; and
a second rod coupleable with the knee alignment hub to be oriented along the tibial axis of the knee,
wherein the proper anatomical angle measured between the first rod and the second rod is less than 180 degrees.

9. A knee alignment system comprising:
femoral cut guide alignment assembly including,
a stationary femoral portion including angular graduations indicative of an angle between a femur and a tibia,
an adjustable medial femoral portion coupled to the stationary femoral portion, and
an adjustable lateral femoral portion coupled to the stationary femoral portion,
wherein a spacing between the adjustable medial femoral portion and the adjustable lateral femoral portion is maintained to provide a known pivot fulcrum between the femoral portions that corresponds to the angular graduations on the stationary femoral portion;
a force sensor coupled to the distal side of the stationary femoral portion; and
a bone interface plate spanning the adjustable medial femoral portion and the adjustable lateral femoral portion to provide protection to a provisionally cut distal femur.

10. The knee alignment system of claim 9, further comprising an electronic display device coupled to the force sensor to display force indications from the force sensor.

11. The knee alignment system of claim 9, further comprising:
a medial adjustable posterior member insertable into a medial posterior longitudinal slot in the stationary femoral portion; and
a lateral adjustable posterior member insertable into a lateral posterior longitudinal slot in the stationary femoral portion;
wherein the medial adjustable posterior member and the lateral adjustable posterior member are configured to abut a provisionally resected posterior portion of the femur.

12. The knee alignment system of claim 9, wherein the medial paddle includes a proximal convex shaped surface;
wherein the later paddle includes a proximal convex shaped surface; and
wherein the proximal convex shaped surfaces create respectively a medial pivot fulcrum and a lateral pivot fulcrum within the femoral assembly.

13. The knee alignment system of claim 12, wherein the femoral cut guide alignment assembly further includes a bone interface plate spanning the medial pivot fulcrum and the lateral pivot fulcrum.

14. The knee alignment system of claim 9, wherein the femoral cut guide alignment assembly further includes a shoulder screw disposed between the adjustable medial femoral portion and the adjustable medial femoral portion and secured to the stationary femoral portion to assist in maintaining the known pivot fulcrum; and
wherein the bone interface plate includes a hole sized larger than the shoulder screw and positioned to accept passage of the shoulder screw when the shoulder screw is secured to the stationary femoral portion.

15. The knee alignment system of claim 9, further comprising a knee alignment verification member coupleable with the stationary femoral portion of the femoral assembly to provide a concurrent visual confirmation of an angle of at least a portion of the femoral cut guide alignment assembly in reference to the femur and the tibia.

16. The knee alignment system of claim 15, wherein the knee alignment verification member includes a laser knee alignment verification member providing a first laser beam oriented along the femoral axis of the knee and a second laser beam oriented along the tibial axis of the knee.

17. The knee alignment system of claim 15, wherein the knee alignment verification member includes a mechanical knee alignment verification assembly, the mechanical knee alignment verification assembly comprising:
a knee alignment hub;
a first rod coupleable with the knee alignment hub to be oriented along the femoral axis of the knee; and
a second rod coupleable with the knee alignment hub to be oriented along the tibial axis of the knee,
wherein the proper anatomical angle measured between the first rod and the second rod is less than 180 degrees.

18. A femoral cut guide alignment assembly removably engageable with a distal end of a femur, the femoral cut guide alignment assembly comprising:
a stationary femoral portion including angular graduations indicative of an angle between the femur and a tibia;
an adjustable medial femoral portion coupled to the stationary femoral portion;
an adjustable lateral femoral portion coupled to the stationary femoral portion,
wherein a spacing between the adjustable medial femoral portion and the adjustable lateral femoral portion is maintained to provide a known pivot fulcrum between the femoral portions that corresponds to the angular graduations on the stationary femoral portion; and
a knee alignment verification member coupleable with the stationary femoral portion of the femoral assembly to provide a concurrent visual confirmation of an angle of at least a portion of the femoral cut guide alignment assembly in reference to the femur and the tibia, wherein the knee alignment verification member includes a laser knee alignment verification member providing a first laser beam oriented along the femoral axis of the knee and a second laser beam oriented along the tibial axis of the knee.

19. A femoral cut guide alignment assembly removably engagable with a distal end of a femur, the femoral cut guide alignment assembly comprising:
- a stationary femoral portion including angular graduations indicative of an angle between the femur and a tibia;
- an adjustable medial femoral portion coupled to the stationary femoral portion;
- an adjustable lateral femoral portion coupled to the stationary femoral portion,
- wherein a spacing between the adjustable medial femoral portion and the adjustable lateral femoral portion is maintained to provide a known pivot fulcrum between the femoral portions that corresponds to the angular graduations on the stationary femoral portion; and a knee alignment verification member coupleable with the stationary femoral portion of the femoral assembly to provide a concurrent visual confirmation of an angle of at least a portion of the femoral cut guide alignment assembly in reference to the femur and the tibia, wherein the knee alignment verification member includes a mechanical knee alignment verification assembly, the mechanical knee alignment verification assembly comprising:
- a knee alignment hub;
- a first rod coupleable with the knee alignment hub to be oriented along the femoral axis of the knee; and
- a second rod coupleable with the knee alignment hub to be oriented along the tibial axis of the knee,
- wherein the proper anatomical angle measured between the first rod and the second rod is less than 180 degrees.

20. A knee alignment system comprising:
femoral cut guide alignment assembly including,
- a stationary femoral portion including angular graduations indicative of an angle between a femur and a tibia,
- an adjustable medial femoral portion coupled to the stationary femoral portion, and
- an adjustable lateral femoral portion coupled to the stationary femoral portion,
- wherein a spacing between the adjustable medial femoral portion and the adjustable lateral femoral portion is maintained to provide a known pivot fulcrum between the femoral portions that corresponds to the angular graduations on the stationary femoral portion;
- a force sensor coupled to the distal side of the stationary femoral portion;

a medial adjustable posterior member insertable into a medial posterior longitudinal slot in the stationary femoral portion; and
- a lateral adjustable posterior member insertable into a lateral posterior longitudinal slot in the stationary femoral portion;
- wherein the medial adjustable posterior member and the lateral adjustable posterior member are configured to abut a provisionally resected posterior portion of the femur.

21. A knee alignment system comprising:
femoral cut guide alignment assembly including,
- a stationary femoral portion including angular graduations indicative of an angle between a femur and a tibia,
- an adjustable medial femoral portion coupled to the stationary femoral portion, the adjustable medial femoral portion including a medial paddle with a proximal convex shaped surface, and
- an adjustable lateral femoral portion coupled to the stationary femoral portion, the adjustable lateral femoral portion including a lateral paddle with a proximal convex shaped surface,
- wherein a spacing between the adjustable medial femoral portion and the adjustable lateral femoral portion is maintained to provide a known pivot fulcrum between the femoral portions that corresponds to the angular graduations on the stationary femoral portion; and
- a force sensor coupled to the distal side of the stationary femoral portion;

wherein the proximal convex shaped surfaces create respectively a medial pivot fulcrum and a lateral pivot fulcrum within the femoral assembly.

* * * * *